US008682685B2

(12) United States Patent
Katz

(10) Patent No.: US 8,682,685 B2
(45) Date of Patent: Mar. 25, 2014

(54) SYSTEM AND METHOD FOR ASSESSING DATA QUALITY DURING CLINICAL TRIALS

(76) Inventor: David P. Katz, Dobbs Ferry, NY (US)

( * ) Notice: Subject to any disclaimer, the term of this patent is extended or adjusted under 35 U.S.C. 154(b) by 960 days.

(21) Appl. No.: 11/577,681

(22) PCT Filed: Feb. 10, 2006

(86) PCT No.: PCT/US2006/004542
§ 371 (c)(1),
(2), (4) Date: Dec. 12, 2007

(87) PCT Pub. No.: WO2006/093645
PCT Pub. Date: Sep. 8, 2006

(65) Prior Publication Data
US 2008/0109455 A1     May 8, 2008

Related U.S. Application Data

(60) Provisional application No. 60/657,386, filed on Mar. 2, 2005.

(51) Int. Cl.
*G06Q 99/00*        (2006.01)
*G06Q 50/00*        (2012.01)
*A61B 5/00*         (2006.01)
*G06F 19/00*        (2011.01)

(52) U.S. Cl.
USPC .......................................................... 705/2

(58) Field of Classification Search
None
See application file for complete search history.

(56) References Cited

U.S. PATENT DOCUMENTS

| | | | |
|---|---|---|---|
| 6,879,970 B2 * | 4/2005 | Shiffman et al. | 706/21 |
| 7,251,609 B1 * | 7/2007 | McAlindon et al. | 705/3 |
| 8,065,180 B2 * | 11/2011 | Hufford et al. | 705/3 |
| 2002/0143563 A1 * | 10/2002 | Hufford et al. | 705/1 |
| 2004/0133450 A1 * | 7/2004 | Foureaux et al. | 705/2 |
| 2005/0203776 A1 * | 9/2005 | Godwin et al. | 705/3 |
| 2007/0150305 A1 * | 6/2007 | Abraham-Fuchs et al. | 705/2 |

* cited by examiner

*Primary Examiner* — Robert Morgan
*Assistant Examiner* — Kristine Rapillo
(74) *Attorney, Agent, or Firm* — Womble Carlyle Sandridge & Rice, LLP

(57) ABSTRACT

The present invention relates to a system and methods for facilitating the improvement of data quality generated during drug and medical device clinical trials. In one embodiment, the invention includes a system and method for generating an ideal subject suitability score for one or more interaction points of a clinical trial. One or more individual subject suitability scores may then be generated from actual subject interaction with the clinical trial for each of the interaction points of the clinical trial. For each interaction point for which an ideal subject suitability score is generated, the one or more individual subject suitability scores may be compared to the ideal subject suitability score to determine the deviation there between. The quality of data collected from actual subject interaction with the clinical trial may be a function of the difference between the individual and ideal subject suitability scores.

33 Claims, 10 Drawing Sheets

SYSTEM AND METHOD FOR ASSESSING DATA QUALITY DURING CLINICAL TRIALS

RELATED APPLICATION

This application claims the benefit of U.S. Provisional Patent Application Ser. No. 60/657,386, filed Mar. 2, 2005, which is hereby incorporated herein by reference in its entirety.

FIELD OF THE INVENTION

The invention relates to a system and method for assessing and facilitating the improvement of data quality generated during drug and medical device clinical trials.

BACKGROUND OF THE INVENTION

The development of a new drug or medical device can be a challenging and time consuming process. If preclinical testing suggests that a promising compound might be well tolerated in humans, it may be tested for safety and pharmacokinetics (drug absorption and metabolism) in healthy volunteers (Phase I). If the results of Phase I trials warrant further investigation, a limited number of patients with the target disease may be challenged with the drug under carefully controlled conditions to evaluate its efficacy and further establish safety and proper dosages (Phase II). If these trials are successful, the drug enters large-scale trials to better characterize its safety and efficacy in patients (Phase III). Typically, clinical trials are coordinated by either contract research organizations (CROs) or academic medical centers that are sponsored by the pharmaceutical manufacturer. Physicians at these institutions conduct the clinical trials and care for the patients/subjects. The Food and Drug Administration (FDA) is the regulatory body having oversight of drug development, which encompasses the preclinical and clinical trial phases of the new drug discovery and testing in humans.

A significant portion of the time and expense of conducting clinical trials arises from the need to assure that the resulting data is accurate. Patients are selected, treated, and evaluated by a meticulous protocol, and the results are usually recorded on standardized forms (case report forms or CRFs) that are collected and analyzed by the sponsor or its designee. To ensure the validity and accuracy of the data, the pharmaceutical company periodically sends a monitor to study sites to verify that patients are treated according to the study protocol and that the information is reported according to the study protocol. Monitoring alone can represent up to 30 percent of the costs of a clinical trial. Most pharmaceutical companies also have separate quality assurance departments to review forms and audit data and safety departments to monitor and prepare reports on adverse events.

From the pharmaceutical manufacturer's perspective, the key issues with respect to data quality and integrity may include how to accurately collect the information that is necessary to assess the safety and effectiveness of the experimental therapy, as well as how to ensure the quality and integrity of that information, while controlling costs and reducing the time consumed by the clinical trial process. From the FDA's perspective, however, the key issue is ensuring that data submitted in support of an application is a valid representation of the clinical trial, especially as the data pertains to drug safety, pharmacokinetics, and efficacy.

Under the Federal Food, Drug, and Cosmetic Act, pharmaceutical manufacturers must obtain a research or marketing permit before beginning studies on certain commodities such as new human drugs, medical devices, veterinary drugs, and food additives. FDA approves these permits, and also regulates biomedical research whose results are then submitted in support of an application for such a permit. The FDA has two principle objectives in regulating this research: 1) to protect the rights and welfare of human research subjects, and 2) to assure the quality and integrity of the biomedical research data used to support the initiation or expansion of clinical trials, the approval of new products and indications, and the labeling of these products.

Pharmaceutical companies monitor and audit clinical trial data: 1) to ensure the safety of the human subjects, 2) to ensure that the company's investment results in a marketable product, and 3) because it is required by the FDA as follows:

Sponsors are responsible for selecting qualified investigators, providing them with the information they need to conduct an investigation properly, ensuring proper monitoring of the investigation(s), ensuring that the investigation(s) is conducted in accordance with the general investigational plan and protocols contained in the IND (Investigational New Drug application), maintaining an effective IND with respect to the investigations, and ensuring that FDA and all participating investigators are promptly informed of significant new adverse effects or risks with respect to the drug . . . 21 C.F.R. 31.250.

Although each company may structure its activities in different ways, responsibility for monitoring is typically distributed as follows. The clinical research department includes medical monitors, often physicians with a considerable amount of clinical experience. The greater burden of monitoring falls to the clinical research associates, who go into the field to make sure that sites are properly initiated and the data are collected appropriately. Most companies also have a separate clinical quality assurance department that conducts in-house file audits to ensure that protocols are written correctly, and conducts site and investigator audits to confirm the qualifications of the investigator, to match case report forms with patient charts, and to review the informed consent forms. Members of the biostatistics and data management group, which is usually separate from the clinical research group, monitor all the data received from the field and investigate emerging trends that might affect safety. The drug safety department collects data on serious adverse effects. Finally, the regulatory affairs group compiles expedited serious adverse effects reports and sends them to the appropriate regulatory agencies.

This process generates an enormous volume of data, and the greater the amount of data that is collected the higher the probability of error. The subsequent task of reconciling the various data streams becomes more difficult.

The reality in clinical drug development is that a clinical trial is only as good as the quality of the data. Under current standards of practice, some of which are regulated, "monitoring" represents an ability to assess study progress but not the quality of the data. The pharmaceutical industry's concept of data quality relates to data entry issues rather than the intrinsic value of the data, i.e., generating experimental results that meet the objectives of the trial. This represents a major drawback in how clinical trials are managed, given time sensitive issues (e.g., patent life) and financial issues (cost of development and recovery of the investment with product launch) that drive this effort. Refocusing the clinical trial development effort to prospectively evaluate the quality of the data without biasing the outcome would provide both time and cost savings.

The protocol of a clinical trial represents a complicated roadmap for trial study. Some studies are of a sufficiently long duration such that they may take months to years to complete. The data that is generated for each of the multiple interaction points in a complicated protocol is fundamental to the successful completion of a clinical trial. The definition of a successful study is one that fulfills the experimental objectives of the protocol, i.e., accurately portrays the safety and efficacy of a new drug or medical device (or the lack thereof). Although the clinical trial protocol may have clear experimental objectives, it is the execution of the protocol which can be variable. Late phase studies or pivotal studies (e.g., Phase 3) can often require 500 to 10,000 study subjects, depending on the indication, to demonstrate safety and efficacy. Generally, this requires multiple investigators and/or study sites to enroll and complete this large number of subjects. In general, the FDA requires that a sponsor of a drug successfully complete two pivotal trials of sufficient magnitude to demonstrate safety and efficacy. As one can imagine, given the challenges of studies of this size, there may be a great variation of interpretation in how study subjects are entered and "complete" the protocol. These discrepancies lead to the generation of data of poor quality and universally delay all clinical drug development programs.

Typically, as a clinical trial goes forward, subject data is collected from a primary source, such as a patient's chart, and transferred to case report forms or other subject data receptacle. At this point, mandated monitoring normally takes place, and upon study subject and/or study completion, the data is entered into a database or other data storage area. In current practice, no attempt is made to assess the value or quality of the collected information until the data is entered into the database alongside various predetermined acceptable ranges for each data variable. Data that is outside the range for each variable may trigger a "data query" to the respective study site for purposes of resolution. If there are enough data queries for a subject that cannot be appropriately resolved, the subject may be invalidated and the subject's data may not be used in the study. Depending on the overall study design, subjects that are invalidated often need to be replaced to meet sample size requirements. This failure to proactively assess data quality while the study is in progress results in budget and timeline deviations because additional subjects need to be obtained and their data collected and analyzed.

These and other problems exist.

SUMMARY OF THE INVENTION

The invention overcomes these and other drawbacks in the management of clinical development programs for new drugs or devices. One aspect of the invention relates to the analysis of the principal components of a clinical study protocol which defines 1) the characteristics of a study subject, 2) the procedures that, if implemented correctly, yield valid and high quality data, and, if desired, other components. Another aspect of the invention relates to the unbiased, real-time review of the data produced during a clinical trial. The invention enables evaluation of data quality as it relates to achieving the clinical objective detailed in the study protocol. An unbiased review indicates that the blind is not broken in a typical double blind, randomized, placebo controlled trial. Quality of the data in this context may include the intrinsic value of the data.

The invention develops a framework or indexing system to assess data quality in a clinical trial, i.e., the intrinsic value of the data in meeting the experimental results that fulfill the objectives of the study, on an ongoing basis. It goes beyond simply evaluating the actual value of the particular variable, whether it is discrete (e.g., yes or no) or continuous data. It evaluates the data quality in the context of the protocol.

In one embodiment, the invention provides a method for assessing data quality of data generated during a clinical trial. In one embodiment, this method includes developing an ideal subject suitability score for one or more interaction points of a clinical trial. The ideal subject suitability score for each interaction point represents a numerical value that defines data of ideal quality for each interaction point of the clinical trial protocol. The ideal subject suitability score may be used as a benchmark for the evaluation of actual patients that are enrolled in the study.

An ideal subject suitability score for an interaction point may be generated by defining data factors that represent the quality variables for the interaction point detailed in the clinical trial protocol. A scoring system may then be associated with each defined data factor. The scoring system may yield an "ideal data factor score" when applied to an "ideal data value" for each data factor. An ideal data value may include a value that signifies ideal data quality for the respective data factor. In some embodiments, ideal data factor scores for each data factor may be weighted according their importance to data quality. These ideal data factor scores may then be utilized to determine the ideal subject suitability score for the interaction point. In one embodiment, the ideal subject suitability score may be an arithmetic sum of weighted ideal data factor scores for the interaction point. In some embodiments, other methods may be used to determine the ideal subject suitability score from the ideal data factor scores.

For each of one or more subjects participating in the clinical trial, an "individual subject suitability score" may be developed for each interaction point of the clinical trial. This individual subject suitability score is based on an individual subject's interaction with the interaction point (e.g., points at which data is recorded from a patient during the clinical trial). Subject interaction with the interaction point may produce "actual data values" for each data factor identified for the interaction point. For each data factor, the scoring system associated with that data factor may be applied to the actual data value, yielding an "actual data factor score." In some embodiments, the actual data factor scores may be weighted according to their importance to data quality. The actual data factor scores may then be utilized to determine the individual subject suitability score for a particular subject's interaction with the interaction point. In one embodiment, the individual subject suitability score may be an arithmetic sum of the weighted actual data factor scores for a subject's interaction with the interaction point. In some embodiments, other methods may be used to determine an individual subject suitability score from the actual data factor scores.

The individual subject suitability score and the ideal subject suitability score may be used to assess the quality of the data from the interaction point. For example, if upon review, an actual subject's individual subject suitability score significantly deviates from the ideal subject suitability score for an interaction point, it may be a real-time "early warning" that data quality is low, that the clinical trial protocol is not being executed properly, and/or other problems.

In another embodiment, the invention provides a method to determine whether a prospective clinical trial site may be suitable for use in an upcoming clinical trial. This method may utilize an ideal subject suitability score representing a study subject having attributes that are likely to produce high quality data. In one embodiment, actual data regarding the prospective study site may be collected such as, for example, historical data of previous trials conducted at the site (which may be indicative of the site's ability to enroll subjects that produce high quality data), population data of the area (which may be indicative of the presence of subjects capable of producing high quality data for the particular clinical trial at issue), and/or other data. This actual data may be utilized to generate a study site aptitude score, which may be compared to the ideal subject suitability score to determine whether the prospective clinical trial site is suitable for use in the upcoming clinical trial.

In another embodiment, the invention provides a method to rapidly determine the acceptability of a potential subject as a candidate for study entry, prior to the potential subject receiving therapy. This method may utilize an ideal subject suitability score that may represent an ideal clinical trial subject having attributes that are likely to produce high quality data. This ideal subject suitability score may be generated by evaluating the key variables in the protocol that are specific to determining subject enrollment to determine data factors, applying scoring systems to these data factors to produce data factor scores, and using these data factor scores to generate the ideal subject suitability score. The scoring systems may then be applied to actual data values gathered from potential clinical trial subjects, to produce individual subject suitability scores. In one embodiment, comparison of the ideal subject suitability score with an individual subject suitability score may indicate a subject's acceptability as a clinical trial candidate.

In another embodiment, the invention provides a method to evaluate the elements of an unsuccessful or otherwise completed clinical trial in order to understand the processes that may have contributed to its failure (or for evaluating other characteristics). This may be accomplished by generating ideal subject suitability scores for one or more interaction points of a completed clinical trial, retrospectively generating individual subject suitability scores for trial subjects based on available data, and identifying what elements of the clinical trial contributed to its failure.

In another embodiment, the invention provides computer-implemented methods, a computer-implemented system, and/or a computer readable medium for performing and enabling the features, functions, and methods described herein.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION OF THE INVENTION

Figure 1:
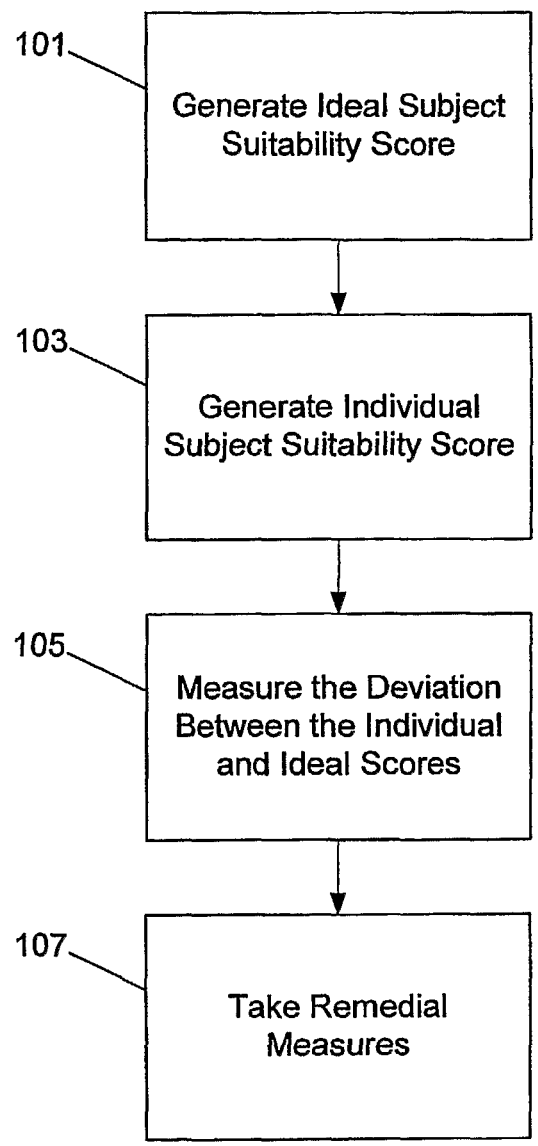
FIG. 1 is an exemplary illustration of a process for assessing clinical trial data quality according to an embodiment of the invention.

The invention provides a system and method for critically assessing the quality of data generated during clinical trials while they are in progress. Quality of data in this context may include the intrinsic value of the data. In one embodiment, the invention enables a user or users to assess the progression of a clinical trial or a clinical development program. In one embodiment, this real-time, proactive assessment of clinical trial progress may include methods that critically review the clinical protocol and accurately define the data factors that govern the production of high quality data. In another embodiment, the invention may forecast the ability of clinical trial investigators or study sites to successfully perform a clinical trial.

Every clinical trial has a protocol which specifies the exact timing and nature of the measurements and/or intervention (e.g., "data collection") to be performed on each patient. A clinical trial protocol may include and/or define a series of "interaction points." An interaction point may include any of the visits or other events within a clinical trial where data is collected from a study subject. A clinical trial subject or "subject," as used herein, may include a human patient or other mammalian subject. While an interaction point may include a subject visit to a hospital or other medical facility for the purposes of administering treatment, collecting data, or other interaction, an interaction point may also take place in other locations or environments (e.g., at the subject's home) and may include any interaction that the subject has with the clinical trial. The timeline of a clinical trial may begin with the screening and enrollment of subjects (the first interaction point) and may continue with one or more subject visits (subsequent interaction points).

The clinical protocol that is written to assess the safety and efficacy of a new drug for a specific disease or indication, in essence, describes a method by which subjects are selected, drug or placebo is administered, safety and efficacy measurements are made and analyzed, and regulatory obligations are met. It is these parameters that define the data that is to be collected from each of the interaction points. As such, data collected for this invention may not only include patient response or physiological reaction to the administration of a treatment, but may include data collected regarding treatment administration (e.g., circumstances of drug administration, etc.), or other data.

Viewed on a strictly operational level, in clinical trial deployment, implementation, and completion, there is an inherent process and a final product: the data. The clinical trial protocol defines a process and a specification for the final product, similar in principle to the manufacture of any finished good. For example, the protocol may contain inclusion and exclusion criteria that define the characteristics of suitable study subjects. The protocol may also define various events and processes for the enrolled subject, including drug administration and clinical or laboratory testing, etc. The end-product of the clinical trial is safety and efficacy data that is generated to answer the experimental questions as defined in the protocol. This safety and efficacy data is usually then recorded in case report forms or in other formats. It is the quality or intrinsic value of this safety, efficacy, or other data product that the invention is concerned with.

According to an embodiment of the invention illustrated in FIG. 1, a method 100 for assessing the quality of clinical trial data is provided. In an operation 101, a review and/or analysis of a clinical trial protocol and/or case report forms may be undertaken to generate an "ideal subject suitability score." The ideal subject suitability score may represent a benchmark for clinical trial data quality when all the data is collected correctly. Each particular interaction point of a clinical trial may have its own ideal subject suitability score, against which actual subject data collected for that interaction point is measured. In some embodiments, some or all interaction points for a clinical trial may be grouped and an ideal subject suitability score may be developed for the group or groups.

The ideal subject suitability score for a particular interaction point may be based at least in part upon the data requirements specified in the trial protocol for that study visit. For example, during the first interaction point of a clinical trial (e.g., the enrollment visit), the specification for the ideal subject suitability score may be determined by the criteria listed in the inclusion and exclusion criteria and the data required for the outcome and safety variables. For subsequent interaction points, the ideal subject suitability score may be based on the detailed study collection needs as found in the protocol (in many clinical trial protocols this information can be categorized as safety and efficacy data).

Figure 2:
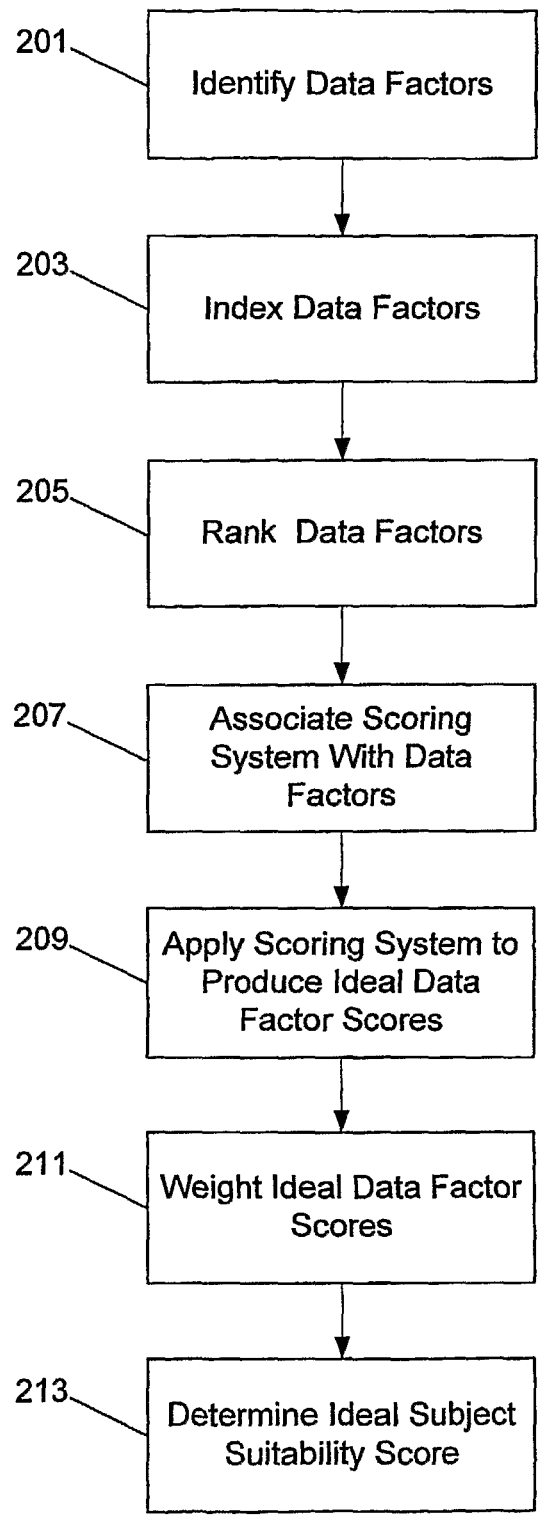
FIG. 2 is an exemplary illustration of a process for generating an ideal subject suitability score according to an embodiment of the invention.

FIG. 2 is an exemplary illustration of a process 200 according to an embodiment of the invention, wherein an ideal subject suitability score for a given interaction point may be generated (as in operation 101 of FIG. 1). In an operation 201, the "data factors" that are to be used for the ideal subject suitability score for the given interaction point may be identified from the clinical trial protocol. In identifying the data factors for an interaction point, the procedures and events involved in subject interaction with the clinical trial protocol may be evaluated. These procedures and events may include enrollment (wherein inclusion and exclusion criteria are utilized), administration of therapy (e.g., administration of drugs, or placebo), observation, clinical and/or laboratory testing (wherein safety and efficacy criteria are utilized), and/or other procedures and events. The quality variables involved with these procedures or events (organized by interaction point) may be utilized to define the "data factors" for an interaction point. The data factors defined for each interaction point may vary depending on the procedures prescribed by the clinical trial protocol.

In some embodiments, multiple data factors may be identified and applied for a procedure or event within an interaction point. These multiple data factors may be used, for example, with procedures or events related to important safety and efficacy measurements. For example, in a trial that involves generation of continuous (as opposed to discrete data, e.g., yes or no) data such as, for example, data derived from clinical laboratory testing, ratings of pathology samples or from endoscopic procedures, various body scans [x-ray, PET scans, MRI, etc.], questionnaires which yield an aggregate score, or other continuous data, multiple data factors that quantify the quality of each of the variables present in the continuous data may be used. These multiple data factors may, for example, correspond to the conditions delineated in the protocol for how measurements are made. For example, for blood tests, the timing of a blood sample relative to administration of a drug/placebo may be an additional factor that is collected (additional to the actual measurement of drug concentration in the blood). Other additional factors may exist such as, for example, were the protocol-specific requirements for testing met, were the samples handled correctly, were appropriately trained personnel involved, or other factors.

In an operation 203, the identified data factors for an individual interaction point may be indexed and/or categorized according to their respective characteristics (e.g., do they deal with inclusion/exclusion, safety, efficacy, or other characteristics; what specific subject interaction procedure or event [e.g., drug concentration measurement] are they associated with). As discussed in detail below, this indexing may aid in selective evaluation of the various components that contribute to overall data quality. In an operation 205, the various data factors may be ranked in order of importance within the given interaction point (or their importance within the subcategories comprising the interaction point, e.g., inclusion/exclusion, safety, efficacy, etc.). In an operation 207, each of the identified data factors for the interaction point may be associated with a scoring system. Different scoring systems may be utilized for different data factors. The scoring system may produce a "data factor score," when applied to a data value for a data factor. Examples of data values may include the absence or presence of a condition (e.g., is the person taking a sample properly trained?), a numerical value regarding subject interaction with the interaction point (e.g., the time period elapsed between a measurement and administration of treatment), or other values.

In an operation 209, the scoring system for each data factor may then be applied to an ideal data value for the data factor to produce an ideal data factor score. Because process 200 deals with generating an ideal subject suitability score, an "ideal data value" indicating the highest possible data quality for the data factor is used. In some embodiments, a range of values may be considered ideal data values. In these embodiments, any data value from the range may be used.

In an operation 211, each ideal data factor score may then be weighted to signify its relative importance to data quality for the given interaction point. Some of the variables represented by the identified data factors may be more indicative of data quality than others, thus, their corresponding data factor scores may be weighted more heavily. Weighting of the data factor score may be dependent on the clinical trial protocol. For example, in some embodiments, a data factor for efficacy may be more heavily weighted for data values representing an on-time measurement, and decrements in data factor score may be more significant. In some embodiments, scoring systems may include exponential or other weighted decrements in data factor score for protocol deviations.

In an operation 213, an ideal subject suitability score may be determined based on the ideal data factor scores. In one embodiment, an arithmetic sum of weighted ideal data factor scores for a given interaction point may be used to generate the ideal subject suitability score for the interaction point. Other methods of determining ideal subject suitability scores from ideal data factor scores may be used. The ideal subject suitability score represents the benchmark against which actual subject data quality may be measured for a specific interaction point.

An example of application of a scoring system in obtaining an ideal subject suitability score may be as follows. For a particular interaction point of a clinical trial, the clinical trial protocol may dictate that a blood sample is required exactly 24 hours after administration of a drug. This blood sample may be utilized to measure the concentration of the drug in the subject's system 24 hours after drug administration. In developing the ideal subject suitability score for this interaction point, a "timing" data factor for this blood collection and drug concentration measurement (there may be many other factors for this collection and measurement) may be identified and associated with a scoring system (as in operation 207). This scoring system may dictate that an ideal data value for this data factor is an elapsed time of 24 hours after drug administration. The scoring system may also dictate that this ideal data value of 24 hours yields a data factor score of 10 and that for each hour deviation (plus or minus) from a precise data value of 24 hours, 0.5 points will be deducted from the perfect data factor score of 10. Therefore, the timing data factor for this blood sample collection may yield an ideal data factor score of 10. This ideal data factor score may then be used (alone or with other ideal data factor scores) to determine the individual subject suitability score.

Figure 3:
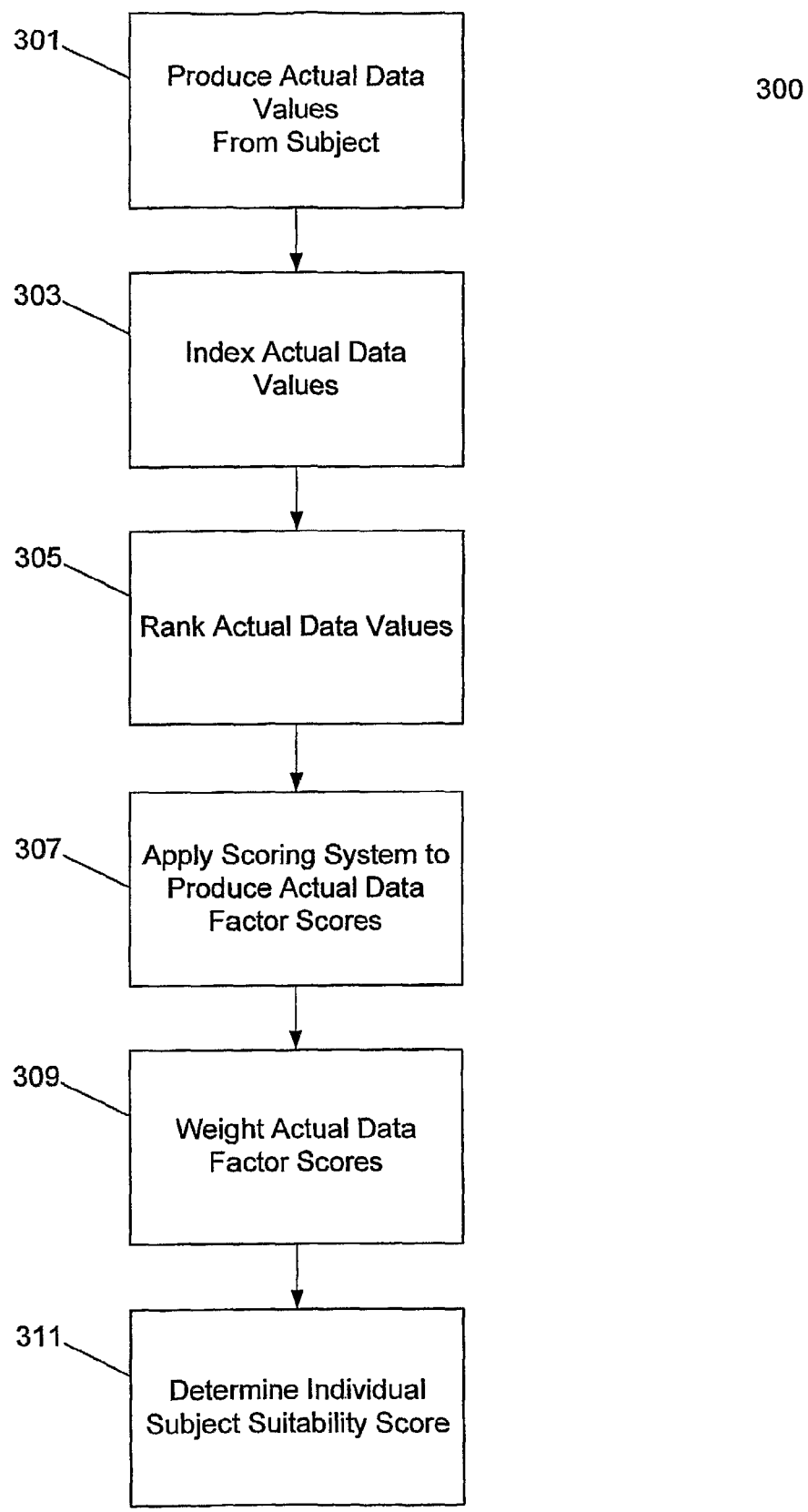
FIG. 3 is an exemplary illustration of a process for generating individual subject suitability scores according to an embodiment of the invention.

Referring back to FIG. 1, an operation 103 may be utilized to generate one or more individual subject suitability scores for a subject participating in the clinical trial. Methods similar to those used to generate the ideal subject suitability score for a particular interaction point may be used to generate individual subject suitability scores for that interaction point. These methods may also be based on the clinical trial protocol. FIG. 3 illustrates an exemplary process 300, wherein an individual subject suitability score may be developed for a specific interaction point of a clinical trial (as in operation 103 of FIG. 1). In an operation 301, actual subject participation/interaction with the procedures or events of the interaction point may be used to produce "actual data values" for each of the one or more data factors that have been identified from the clinical trial protocol for the interaction point. In one embodiment, the actual data values for each data factor may be collected and recorded.

In an operation 303, the actual data values for each data factor may then be indexed according to the index developed for the ideal subject suitability score of the interaction point. In an operation 305, the actual data values may be ranked according to the ranking system developed for the data factors of the ideal subject suitability score. In an operation 307, the scoring system associated with each data factor may be applied to the actual data value for that data factor. Applying this scoring system may produce "actual data factor scores." In an operation 309, the actual data factor scores may then be weighted according to the same weighting system that were used for the data factors in the calculation of the ideal subject suitability score for the interaction point.

In an operation 311, the individual subject suitability score may then be determined from the actual data factor scores for an individual subject's interaction with the interaction point. The individual subject suitability score represents a measure of the quality of data obtained for an individual clinical trial subject for the interaction point. In some embodiments, an arithmetic sum of weighted actual data factor scores may be utilized to determine the individual subject suitability score. Other methods of determining individual subject suitability scores from actual data factor scores may be used. However, the method used to determine an ideal subject suitability score for an interaction point, will parallel the method used to determine the individual subject suitability scores for the interaction point (as they both are derived from the same clinical trial protocol).

An example of applying a scoring system to actual data values may be seen by revisiting the blood collection example given above. An actual data value for the timing data factor described above may equal 24 hours (i.e., blood collection 24 hours after drug administration). Under the scoring system described above, this actual data value of 24 hours will yield a perfect actual data factor score of 10. However, if the blood sample was collected from a subject 25 hours after administration of the drug, the actual data value for the subject would be 25 hours. Under the scoring system, a 25 hour actual data value will yield a 9.5 actual data factor score (because of the 0.5 deduction in data factor score for every hour deviation from the ideal data value). This actual data value score of 9.5 may be used (alone or with other actual data factor values) to determine the subject's individual subject suitability score. In an instance in which no blood was drawn for this measurement, the actual data value for this data factor may be zero. Therefore, applying the scoring system to an actual data value may yield an actual data factor score of zero.

In an operation 105, a data quality assessment may be generated for an interaction point using one or more of the individual subject suitability scores for the interaction point and the ideal subject suitability score for the interaction point. This data quality assessment may reflect the data quality of a single clinical trial subject (if only one individual score was used) or of many subjects (if multiple individual scores were averaged and used). In some embodiments the data quality assessment may be generated by comparing the one or more individual subject suitability scores of an interaction point to the ideal subject suitability score of the interaction point. In some embodiments the deviation of an individual subject suitability score from an ideal subject suitability score may be indicative of data quality of the data corresponding to the individual score. In some embodiments, the greater the individual score deviates from the ideal score, the poorer the quality of the data.

This data quality assessment enables real-time, proactive monitoring and assessment of the quality of the data collected from the individual subjects participating in the trial. This monitoring and assessment enables timely remediation or other measures to be taken regarding the investigators, the study sites, the protocol, and/or the clinical trial as a whole.

In some embodiments, individual and ideal subject suitability scores may be utilized for one or more data mining processes. For example, in some embodiments (as described above), the quality of data for individual subjects at individual interaction points may be assessed by comparing an individual subject suitability score of a subject at a particular interaction point to the ideal subject suitability score for that interaction point. In other embodiments, individual subject suitability scores may be aggregated and/or averaged and compared to the ideal subject suitability score for a particular interaction point. This may enable assessment of the data quality of some or all subjects in a clinical trial for that interaction point. In some embodiments, interaction points may be grouped and ideal and individual subject suitability scores may be used to assess the quality of data resulting from some or all interaction points in a clinical trial. In some embodiments, individual subject suitability scores may be grouped by trial site to measure a particular site's data quality. Other selective data categorizations, assessments an/or data mining may be performed.

In an operation 107, after data quality for the data of interest has been measured, remedial measures may be generated and/or performed. Remedial measures may include, for example, adjusting the clinical trial protocol, re-training personnel who collect data (or other persons involved in conducting the clinical trial), shutting down a study site, shutting down the trial altogether, or other measures.

Assessing data quality according to the invention may not necessarily involve judgment of the actual measurements obtained from subject interaction with the clinical trial. The methods of the invention do not evaluate the fact that a measurement may represent good or bad news to the sponsor of the clinical trial (e.g., too much, too little, or just enough of a physiological response in the patient's system). However, if, for example, a sample was taken too early or too late, the actual measurement data may be of poor quality and thus of little importance to the clinical trial because the measurement was obtained through a deviation from the clinical trial protocol. The methods described herein assess this data quality.

One of the problematic issues that affects clinical trials may include subject-specific quality issues. Subject-specific quality issues routinely include whether the subjects enrolled in the study are suitable for study entry. The invention may aid in the alleviation of these subject-specific issues.

The specification for subject suitability may be detailed by the inclusion and exclusion criteria for the particular trial. This may be a literal checklist of characteristics that are appropriate (inclusion criteria) or inappropriate (exclusion criteria) for subjects in the clinical trial. An ideal subject may receive all affirmatives for inclusion and all negatives for exclusions. Subjects that do not meet this ideal specification may not be suitable for study entry. This may be where the problem in clinical trial data quality begins.

To help illustrate the subject-specific quality issues, an example of the inclusion/exclusion criteria for a drug trial is detailed below:

A Randomized, Multi-Center, 8 Week, Double-Blind, Placebo-Controlled, Flexible-Dose Study to Evaluate the Efficacy and Safety of Drug X in Children and Adolescents with Major Depressive Disorder (MDD)

Inclusion Criteria:
   Male or female patients age 7 years 0 months to 17 years 11 months inclusive.
      Yes ☐ No ☐
   Diagnosis of MDD, either single episode or recurrent according to DSM-IV (296.2 or 296.3, respectively) confirmed by the Kiddie-Sads-Present and Lifetime version (K-SADS-PL) semi-structured interview
      Yes ☐ No ☐
   Patients with a total raw summary score of 45 or greater on the Children's Depressive Rating Scale-Revised (CDRS-R) at the Screening and Baseline Visits.
      Yes ☐ No ☐
   Custodial parent's or legal guardian's written informed consent before performance of any study-specific procedures and patient's assent and/or consent where required.
      Yes ☐ No ☐
Exclusion Criteria:
   Patients who in the investigator's judgment present with a clinically predominant Axis I disorder other than MDD.
      Yes ☐ No ☐
   Patients with any history of psychotic episode or psychotic disorder.
      Yes ☐ No ☐
   Patients with a history of Bipolar Disorder.
      Yes ☐ No ☐
   Patients with mental retardation.
      Yes ☐ No ☐
   Patients diagnosed with Substance Abuse or Dependence within 3 months prior to screening.
      Yes ☐ No ☐
   Patients who tested positive for illicit drug use at the Screening visit.
      Yes ☐ No ☐
   Patients who, in the investigator's judgment, posed a suicidal or homicidal risk.
      Yes ☐ No ☐
   Patients who have taken other psychoactive drugs with in the time frames specified below prior to the screening visit:
   Fluoxetine, MAOIs—4 weeks or less
      Yes ☐ No ☐
   Depot antipsychotics—12 weeks or less
      Yes ☐ No ☐
   Antidepressants other that MAOIs or fluoxetine, etc.—14 days or less.
      Yes ☐ No ☐
   Hypnotics, benzodiazepines, and all other sedatives (including sedating antihistamines)—5 half-lives or 14 days (whichever is longer) or less.
      Yes ☐ No ☐
   Any CNS-active herbal/natural supplement or preparation known or thought to have any psychoactive effects—14 days or less
      Yes ☐ No ☐
   Patients with epilepsy.
      Yes ☐ No ☐
   Patients who, in the opinion of the investigator, would be non-compliant with the visit schedule or other study procedures
      Yes ☐ No ☐
   Patients with clinically significant abnormalities in hematology, blood chemistry, ECG, or physical examination at Screening that was not resolved by the Baseline visit.
      Yes ☐ No ☐
   Patients with known hypersensitivity to SSRIs
      Yes ☐ No ☐
   Patients who had electroconvulsive therapy with 3 months of Screening
      Yes ☐ No ☐
   Female patients who had a positive serum HCG pregnancy test or who were lactating
      Yes ☐ No ☐
   Sexually active female patients who were not using a reliable method of contraception
      Yes ☐ No ☐
   Patients who received any investigational drug within 6 months of Screening
      Yes ☐ No ☐
   Patients requiring concurrent psychotherapy.
      Yes ☐ No ☐
   Patients who, in the judgment of the investigator, had a clear history of non-response to SSRI treatment for their MDD, defined as a non-response to at least two different SSRIs following adequate courses of treatment (i.e., received recommended doses for 4 to 6 weeks for each)
      Yes ☐ No ☐

Since this exemplary study is a study of the effect of treatment of an experimental drug on major depressive disorder (MDD) in children and adolescents, it may be essential that each proposed subject meet these inclusion criteria. Therefore, the subjects must be age appropriate, have a diagnosis of MDD, and meet the stringent criteria set by using the defined method of measuring depression and having a score as defined in the protocol. In an embodiment of the invention, the data factors (or their resultant data factor scores) for these criteria may be heavily weighted. In this example, the inclusion requirement for parental or guardian consent may be essential for legal purposes. However, in regards to scoring under the present invention, this requirement may not be weighted as heavily as the three other inclusion criteria, because it may be thought to have little effect on the quality of the subsequent data collected.

In regards to exclusion criteria, all of the 23 requirements barring entry to the study listed above are important; however, some may be more significant than others, and thus, may be weighted more than others. Any patient characteristic that will impact negatively on the trial and that is met by the subject will cause the individual subject suitability score to drop. In this example, subjects with increased risk for suicide who have taken drugs that may interfere with the experimental therapy within a defined time period will cause a negative deflection on those subjects' individual subject suitability scores for the enrollment interaction point. Accordingly, subjects who have a concomitant condition which may affect study results will also cause a negative deflection on those subjects' individual subject suitability score for the enrollment interaction point. It may be determined that these characteristics will be weighted more negatively in the subjects' individual subject suitability scores since these conditions may have been determined to substantially decrease data quality through their unique negative impact on accuracy of the collected data.

Other issues that affect the quality of clinical trial data are operational issues. These operational problems revolve around the actual implementation of a clinical trial's protocol. The invention may aid in assessment and resolution of these operational issues.

A typical protocol may describe exactly when subjects receive treatments and the battery of safety and efficacy testing they undergo before, concurrent to, and/or after such treatments. The uniformity of these procedures is important since hundreds of subjects are studied at multiple study sites, and successful measurement of the effects of an experimental drug versus placebo depends on proper execution of trial protocol. An example of evaluation criteria (safety and efficacy measures) for a given protocol is found below:

Evaluation Criteria

Efficacy Parameters:
The primary efficacy variable is the change from baseline in the CDRS-R total score. The score will be assessed baseline and four and eight weeks after randomization to therapy.
The secondary efficacy variable is the change from baseline in the Clinical Global Impression (CGI) Severity of Illness item score. The score will be assessed baseline and four and eight weeks after randomization to therapy.
Safety Parameters:
Safety will be assessed by 1) adverse event monitoring, 2) vital signs, 3) laboratory evaluations, 4) serum pregnancy tests, 5) ECGs, and 6) physical examinations. Measurements will be made at baseline and four and eight weeks after randomization to therapy.

The goal in this exemplary trial is to demonstrate that the experimental drug is useful in treating MDD in pediatric and adolescent subjects, and that there are no unacceptable safety risks. The efficacy measure is made by using a standardized assessment tool that is used to measure depression before, during, and after treatment. The safety determination is made using a standard battery of tests that are performed before, during and after treatment. To assess the quality of the data without biasing the outcome of the trial, the method of the present invention looks at the particular data points that need to be collected, but does not evaluate the data in the larger picture, i.e., is the drug safe and effective.

For example, the primary measurement of efficacy (e.g., the primary efficacy variable) for this study is the CDRS-R total score, which needs to be collected at specific time points after the drug has been administered, i.e., four and eight weeks into the study. To assess the quality of this important variable, the following questions may be devised and utilized to develop data factors for each of the various interaction points of the trial: 1) Was the CDRS-R assessment tool administered by the designated individual trained in using the test? 2) Was the measurement successfully completed? 3) Was the data collected? 4) Was the data collected within the correct time interval as specified by the protocol? 5) Is the resulting data within the expected range for the particular variable(s)? All five of these data factors illustrate how additional or multiple data factors may exist for each singular measurement, or patient interaction.

Based upon the answers to the above questions, the quality of the CDRS-R score may be measured at each interaction point and the quality of those measurements may be quantified within the methods of the invention. This may be accomplished by determining the actual data values for the data factors for each interaction point (baseline, four weeks, eight weeks), obtaining actual data value scores by applying a scoring system to the actual data value scores, weighting the actual data value scores according to their respective importance to data quality for each interaction point, adding the weighted actual data value scores for each individual at each interaction point to produce individual subject suitability scores (e.g., FIG. 3), comparing those scores to pre-calculated ideal subject suitability scores (according to the methods described herein, e.g., FIGS. 1 & 2), and measuring the deviation between the individual subject suitability scores and the ideal subject suitability scores (e.g., FIG. 1).

Each critical safety or efficacy variable can be similarly broken down into the data factors that determine the quality of the collected data. The following questions illustrate an example of criteria that may be utilized to define the quality of a discrete measurement under consideration (and thus develop data factors for the methods of invention): 1) Was the data collected? 2) Was the data collected within the correct time interval as specified by the protocol? 3) Is the resulting data within the expected range for the particular variable(s)? Depending on the requirements for each clinical trial protocol, and the nature of the measurements being made, different additional factors may be required to develop data factors that represent the issues of data quality for a particular variable.

Figure 4:
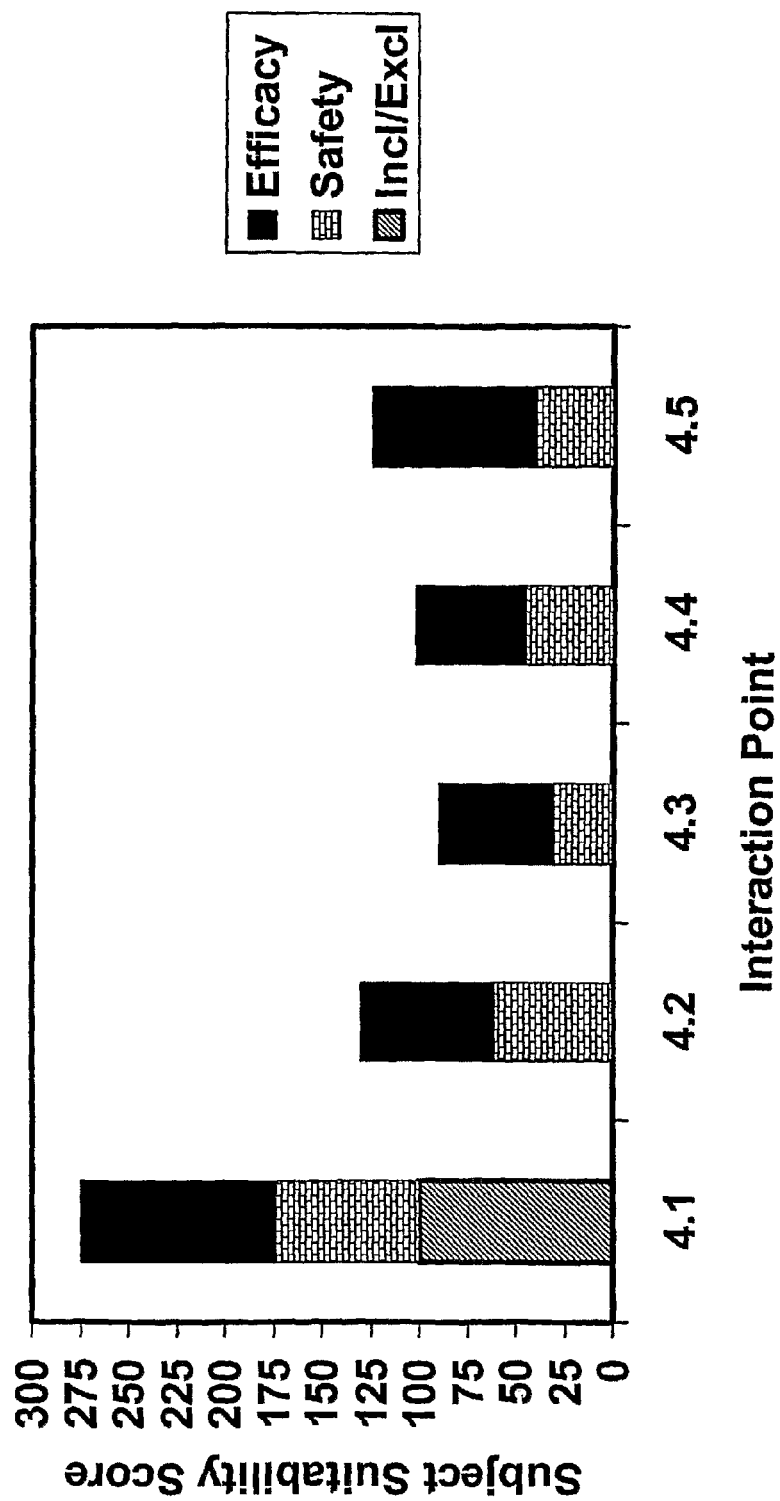
FIG. 4 is an exemplary bar graph showing category defined ideal subject suitability scores by visit.

FIG. 4 is an exemplary illustration of ideal subject suitability scores generated for five interaction points of a clinical trial using inclusion/exclusion, safety, and efficacy data for a clinical trial. The ideal subject suitability scores are based upon the data requirements for each protocol directed interaction point. For example, during an interaction point 4.1 (the enrollment visit), the ideal subject suitability score may be determined by the criteria listed in the inclusion and exclusion checklist and the baseline data required for the safety and efficacy variables. For interaction points 4.2 through 4.5, the ideal subject suitability scores may be based on the detailed study collection needs as found in the protocol that define the requirements for safety and efficacy data. Depending on the study and its data requirements, there may be additional data factors that are considered for quality calculation with regard to a specific measurement or interaction.

FIG. 4 illustrates one way the different categories (e.g., inclusion/exclusion, safety, efficacy, or other categories) of data comprising the overall ideal subject suitability score for an interaction point may be identified and differentiated. This identification and/or differentiation may relate to, or result from, indexing of data factors used in generation of ideal subject suitability scores (such as, for example the indexing performed in operation 203 of FIG. 2). FIG. 4 also illustrates that the relative contribution of the constituent data categories to that interaction point's ideal subject suitability score, may be also identified, visualized, and/or utilized. For example, for interaction point 4.1, inclusion/exclusion criteria comprise about 100 points of the 275 point overall ideal subject suitability score. Safety criteria contribute 75 points to the ideal subject suitability score, while efficacy criteria contribute 100 points.

Figure 5:
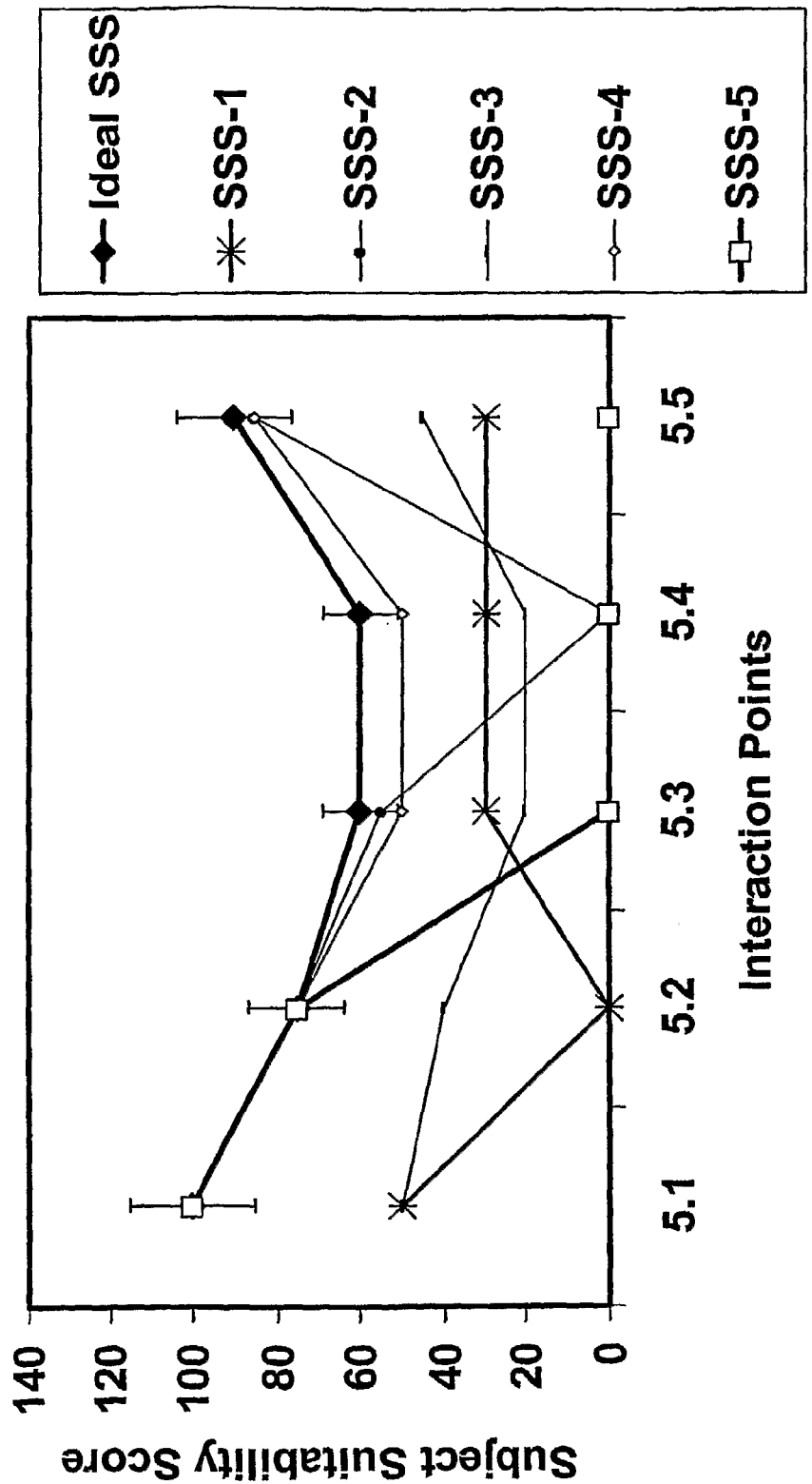
FIG. 5 is an exemplary graph showing aggregate subject suitability score by visit of an ideal subject (Ideal SSS) versus ten actual subjects (SSS-1 to SSS-5).

FIG. 5 is an exemplary illustration according to an embodiment of the invention, wherein ideal subject suitability scores are compared to several individual subject suitability scores over the course of interaction points 5.1 to 5.5. As detailed above, similar methods may be utilized to calculate the individual subject suitability scores (e.g., SSS-1, SSS-2, etc.) as are used to determine the ideal subject suitability score (e.g., Ideal SSS). The deviation of individual subject suitability scores from the ideal subject suitability score for each interaction point results in a measure of the quality of the data for each interaction point.

From the data displayed in FIG. 5, it is apparent that some subjects are missing their study visits/interaction points (or the data is being collected with startling deviation from the protocol) and as such, are given a subject suitability scores of zero for that interaction point (e.g., SSS-1 for interaction point 5.2; SSS-5 for interaction points 5.3 through 5.5). By reviewing the data for interaction point 5.1 (the enrollment visit), it is apparent that this study site is not enrolling subjects that match the inclusion/exclusion criteria for the protocol, given the low subject suitability scores of SSS-1 and SSS-3. In subsequent interaction points 5.2 through 5.5 the data quality for several subjects is unsatisfactory given the low individual subject suitability scores (e.g., SSS-3 for interaction points 5.2, 5.3, 5.4 and 5.5). The precise range for what deviation in subject suitability scores is acceptable may vary among clinical trials and/or interaction points.

As mentioned above, the degree of deviation in individual subject suitability scores, aggregate individual subject suitability scores, or study site aggregate scores may have a predictive value on the ability of the investigator or site to perform the clinical trial. For example, if a study site or an investigator has too many actual subjects whose individual subject suitability scores deviate from the ideal subject suitability score, it is unlikely that these subjects will meet the clinical objectives of the protocol since the data will be of poor quality. On the contrary, if a study site has subjects whose individual subject suitability score closely tracks the ideal subject suitability score, it is likely that these subjects will meet the clinical objectives of the protocol and the data will be of high quality.

Figure 6:
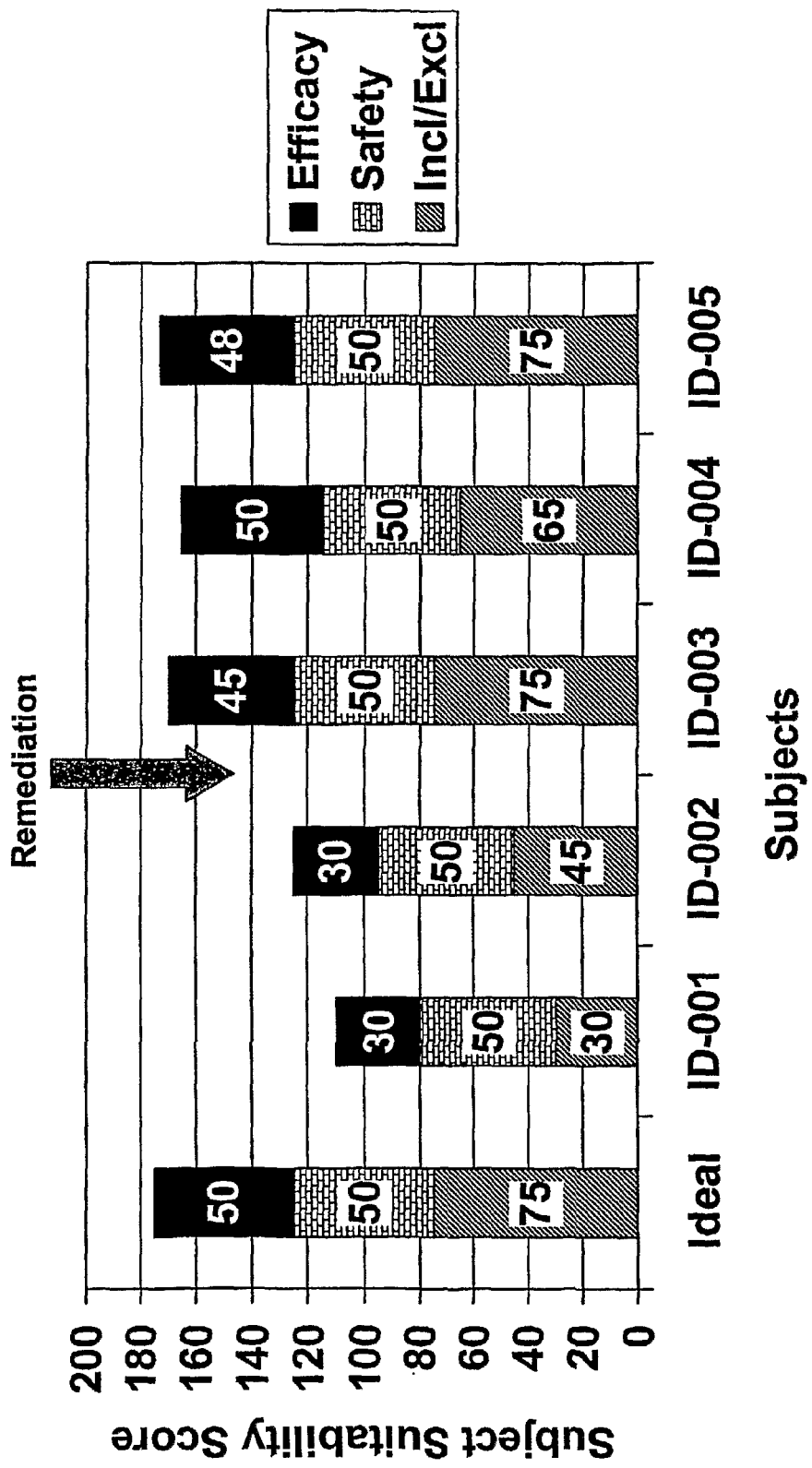
FIG. 6 is an exemplary bar graph showing category defined subject suitability score enrollment visit of ideal versus actual subjects.

FIG. 6 is an exemplary illustration according to an embodiment of the invention, wherein an ideal subject suitability score is compared to individual subject suitability scores for a single interaction point. The ideal and individual subject suitability scores illustrated in FIG. 6 are broken down by the categories of data factors utilized for that particular interaction point. In this case, the particular interaction point analyzed is the enrollment visit. As such, the data categories include the inclusion/exclusion data, the baseline safety data, and the baseline efficacy data. Breaking down subject suitability scores, as illustrated in FIG. 6, may enable a systematic review of potential problem areas for this particular data point. In some embodiments, for analysis or other purposes, the ideal, individual, and/or aggregate subject suitability scores for one or more interaction points may be broken down in different ways such as, for example, by individual data factors, by individual subject interaction, or by other characteristics.

In viewing the example of FIG. 6, it is evident that the study site is initially having difficulties in the enrollment of study subjects (as evidenced by the low inclusion/exclusion scores for ID-001 and ID-002). In this example, the lower portion of each bar in the bar graph represents a quality assessment of the inclusion and exclusion data. The first two subjects enrolled (ID-001 and ID-002) are well below the requirement of the ideal subject and will not be considered suitable subjects.

In this example, the topmost portion of each bar represents the baseline measurements to determine efficacy. As such, ID-001 and ID-002 also have scores that are well below the efficacy requirements for a suitable subject. The precise range for what deviation in subject suitability scores is acceptable may vary among clinical trials. In this example 30 out of 50 for efficacy data may be thought to be unacceptable.

It also appears that the exemplary study site illustrated in FIG. 6 is not having difficulty performing the safety related measures. However, this will not be enough to offset the difficulties in meeting the inclusion/exclusion and efficacy criteria.

The illustration of the invention in FIG. 6 illustrates the fact that the invention enables real-time, prospective review of information. Thus, providing an "early warning" to the study sponsor about the qualifications, capabilities, and/or aptitude of the clinical investigator, the study site, and/or the study protocol itself. In some circumstances, the study sponsor may elect to close down the site. In other circumstances, the study sponsor may choose to implement a remediation program such as, for example, re-training the site staff so they increase their compliance with the study protocol. In the example of FIG. 6, a remediation program was initiated after the enrollment of subject ID-002. Subsequently enrolled subjects had an improved subject suitability score resulting in higher quality data.

Properly screening subjects for a clinical trial may be a critical first step in ensuring that a study protocol will be executed correctly. Deciding whether a potential investigator and/or the study site will have an acceptable patient population to fulfill the requirement of a protocol is more difficult. Traditionally, when the sponsor of a clinical trial or its representative contract research organization (CRO) is identifying potential investigators or sites for a drug study they often rely on a non-systematic approach for determining the capability of the investigator or site to supply appropriate subjects. The net result is that sites that appeared promising often times do not deliver the enrolled and completed study subjects as promised. In one embodiment, the invention offers a more rigorous method for qualifying study sites to participate in a drug study and to aid in the prospective evaluation of potential study subjects.

Figure 7:
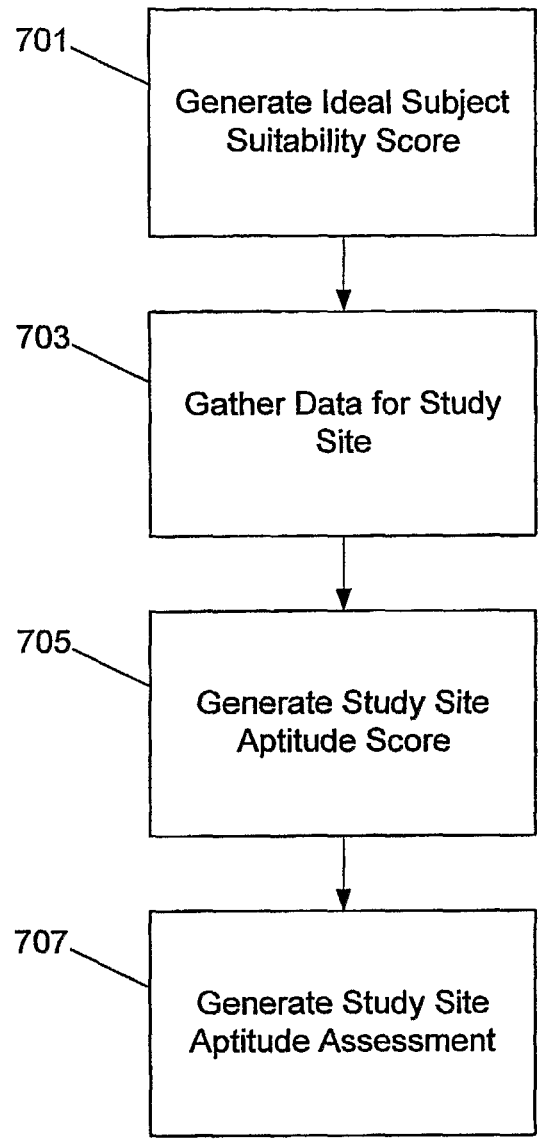
FIG. 7 is an exemplary illustration of a process for evaluating a potential clinical trial site according to an embodiment of the invention.

In one embodiment, as illustrated in FIG. 7, a method 700 is provided to determine if the site has access to, or is capable of enrolling clinical trial subjects that are likely to produce high quality data. In an operation 701, an ideal subject suitability score for an ideal subject participant may be generated. This ideal subject suitability score may be based on data factors that concentrate on exclusion and inclusion criteria according to the protocol of the clinical trial. This formulation may involve operations similar to the development of ideal subject suitability scores as described in the methods above (e.g., identification of data factors, indexing of data factors, ranking of data factors, associating scoring systems with data factors, applying the scoring systems, weighting the resultant ideal data factor scores, summing the weighted ideal data factor scores, and/or other operations).

In an operation 703, historical data regarding previous studies conducted at the proposed site (which may be indicative of the site's ability to enroll subjects that produce high quality data), population data for the area surrounding the study site (which may be indicative of the presence of subjects capable of producing high quality data for the particular clinical trial at issue), and/or other data may be gathered. In an operation 705, the data from operation 703 may be used to generate a study site aptitude score. The study site aptitude score may be generated by identifying the actual historical, population, and/or other data values that corresponds to the data factors identified in the formula used to develop the ideal subject suitability score of operation 701. This "identified data" may then be applied to the index/scoring/weighting procedures used to develop the ideal subject suitability score. For example, application of scoring systems associated with the data factors to actual data values derived from the "identified data" may yield study site data scores. These study site data scores may be weighted and/or otherwise used to determine the study site aptitude score. In an operation 707, a study site aptitude assessment may be generated. The study site aptitude assessment may reflect the study site's access to, and/or ability to enroll clinical trial subjects likely to yield high quality data. In one embodiment, the study site aptitude assessment may be generated by comparing the study site aptitude score to the ideal subject suitability score. The deviation between the two scores may be used to determine the study site aptitude assessment for the proposed study site.

Figure 8:
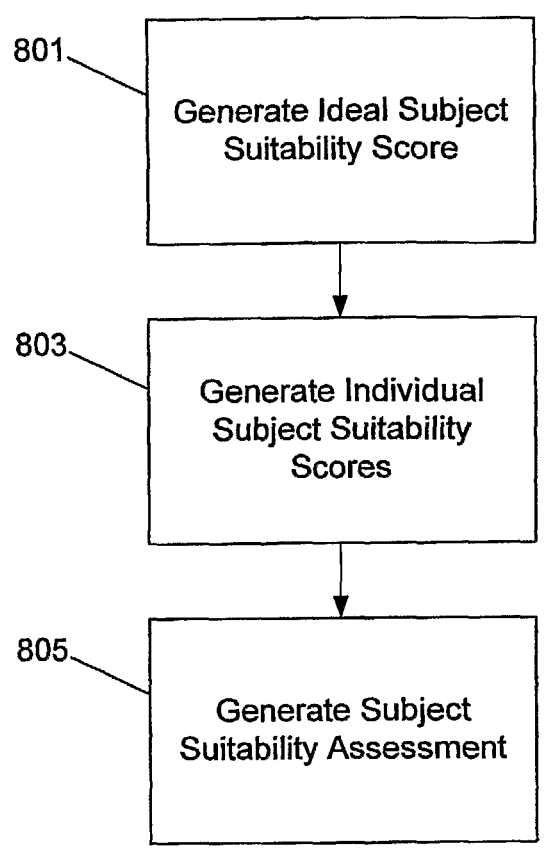
FIG. 8 is an exemplary illustration of a process for evaluating subject suitability according to an embodiment of the invention.

In an embodiment illustrated in FIG. 8, a method 800 according to an embodiment of the invention is provided, wherein the acceptability of a potential subject as an entrant to the study may be determined prior to the potential subject receiving therapy. In an operation 801, an ideal subject suitability score may be generated. Operation 801 may utilize inclusion and exclusion criteria detailed in the clinical trial's protocol. The development of the ideal subject suitability score of operation 801 may involve operations similar to the development of ideal subject suitability scores as described in the methods above (e.g., identification of data factors, indexing of data factors, ranking of data factors, associating scoring systems with the data factors, applying the scoring systems, weighting the resultant ideal data factor scores, summing weighted ideal data factor scores, and/or other operations).

In an operation 803, individual subject suitability scores may be generated, prior to enrollment, by collecting actual inclusion/exclusion data from potential subjects. This generation may involve operations similar to the development of individual subject suitability scores as described in the methods above (e.g., correlating actual data values to identified data factors, ranking actual data values, applying scoring systems, weighting resultant actual data factor scores, summing weighted actual data factor scores, and/or other operations). In an operation 805, a subject suitability assessment may be generated. The subject suitability assessment may reflect an individual potential clinical trial subject's potential to produce high quality data. In some embodiments, the subject suitability assessment may be generated by comparing an individual potential subject's individual subject suitability score to the ideal subject suitability scores. As such, the aptitude of individual potential subjects (or groups thereof) may be judged.

Figure 9:
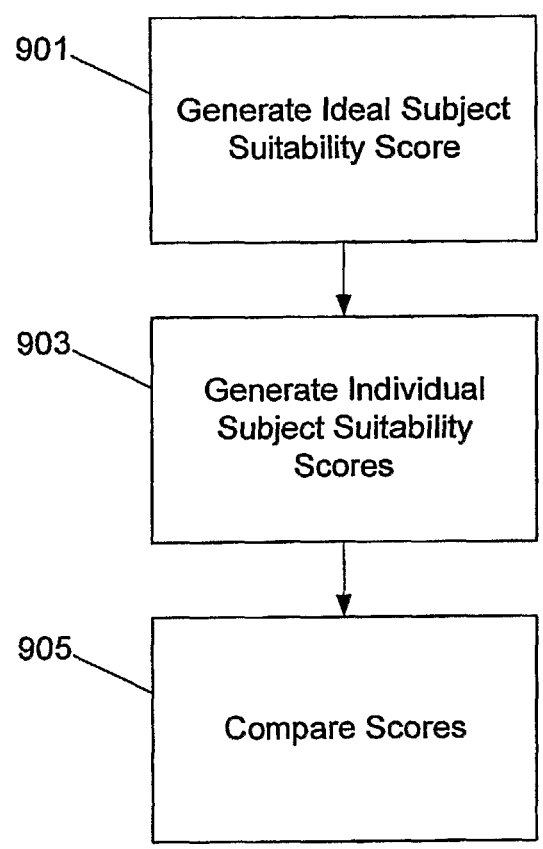
FIG. 9 is an exemplary illustration of a process for evaluating a completed clinical trial according to an embodiment of the invention.

Clinical trials of new drugs can often fail in late stage development, despite success at earlier phases. Given the expense of repeating a large clinical trial, a method by which a completed trial could be systematically reviewed may aid a drug or medical device sponsor in deciding whether or not they should commit to performing another large multi-center trial. In one embodiment of the invention illustrated in FIG. 9, a process 900 for evaluating a completed trial is provided. In an operation 901, the protocol of a completed clinical trial may be utilized to generate ideal subject suitability scores for one or more interaction points of the completed clinical trial. This score generation may involve operations similar to the development of ideal subject suitability scores as described in the methods above (e.g., identification of data factors, indexing of data factors, ranking of data factors, associating scoring systems with the data factors, applying the scoring systems, weighting resultant ideal data factor scores, summing weighted data factor scores, and/or other operations).

In an operation 903, individual retrospective subject suitability scores may be generated using available subject interaction data. This development may involve operations similar to the development of individual subject suitability scores as described in the methods above (e.g., correlating actual data values to identified data factors, ranking actual data values, applying scoring systems, weighting resultant actual data factor scores, summing weighted actual data factor scores, and/or other operations). In an operation 905, the individual scores may be compared to the ideal scores to assess the quality of the data acquired from the completed clinical trial. Process 900 may enable various selective/differential groupings and comparisons between ideal and individual scores that may be utilized for data mining of the quality of data for a completed clinical trial. This data mining may enable identification of one or more characteristics of the completed clinical trial, including, for example, elements that caused the failure of the completed clinical trial.

Those having skill in the art will appreciate that the processes of the invention described herein may work with their constituent operations performed in varying orders. Accordingly, some or all of the operations described herein may be used in various combinations to perform the processes of the invention.

Figure 10:
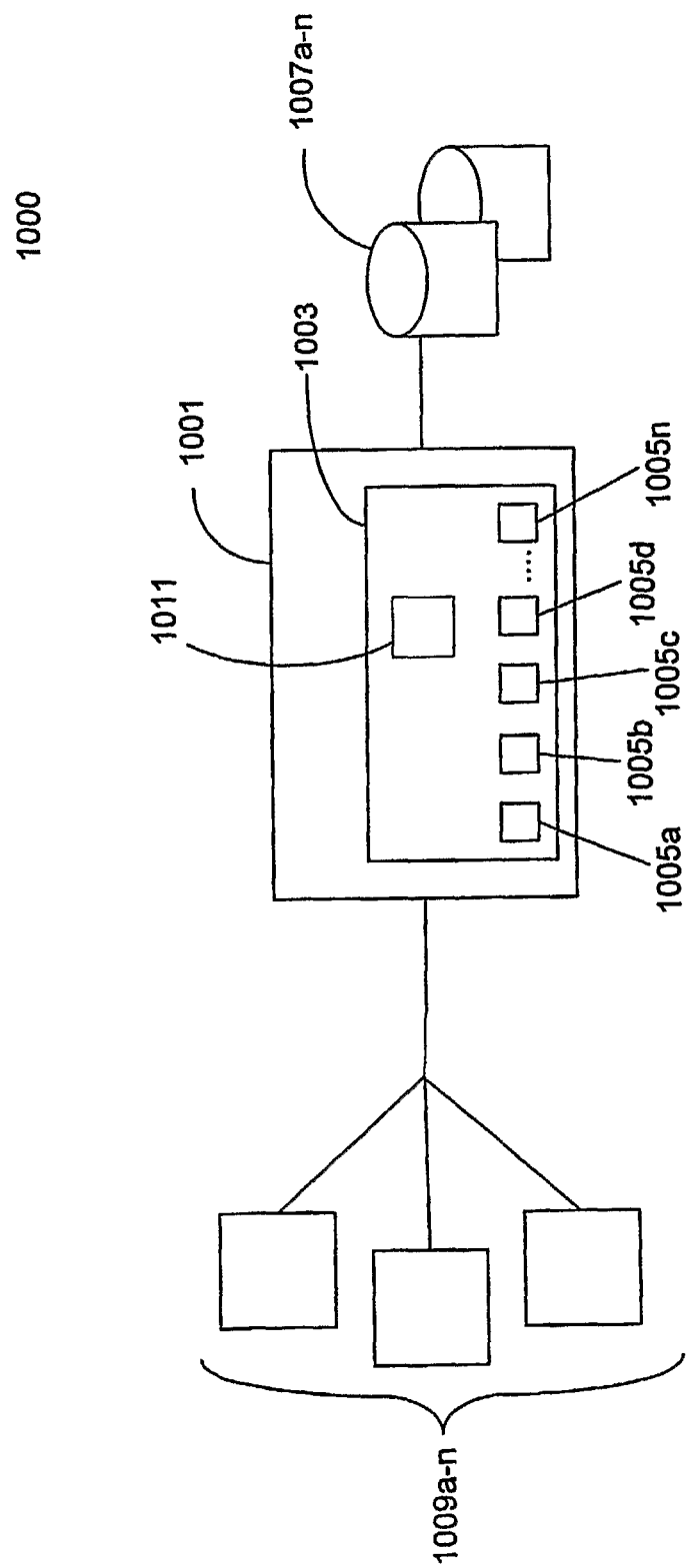
FIG. 10 is an exemplary computer-implemented system according to an embodiment of the invention.

According to an embodiment of the invention illustrated in FIG. 10, the invention provides a computer-implemented system 1000 that enables performance of the data quality assessment features and other features described herein. Computer implemented system 1000 may include a computer system 1001, a data quality application 1003, one or more software modules 1005a-n, a data storage devices 1007a-n, one or more terminal devices 1009a-n, and/or other elements.

Computer system 1001 may include one or more personal computers, laptop computers, servers, or other machines which may be or include, for instance, a workstation running Microsoft Windows™ NT™, Microsoft Windows™ 2000, Unix, Linux, Xenix, IBM, AIX™, Hewlett-Packard UX™, Novell Netware™, Sun Microsystems Solaris™, OS/2™, BeOS™, Mach, Apache, OpenStep™, or other operating system or platform. Computer system 1001 may include one or more processors 1011 which may receive, send, and/or manipulate data for the performance of the features, functions, and or operations of the invention as described herein, including the any or all of the operations of the methods described in FIGS. 1, 2, 3, 7, 8, 9 and/or other methods.

According to one embodiment, computer system 1001 may host a data quality application 1003. Data quality application 1003 may comprise a computer application maintained by an clinical trial sponsor, a clinical trial administrator, a research services provider, or other entity.

According to an embodiment of the invention, data quality application 1003 may include or comprise one or more software modules 1005a-n for generating ideal subject suitability scores, generating individual subject suitability scores, analyzing clinical trial protocols, identifying data factors, correlating data values (actual or ideal) to identified data factors, indexing data factors or data values, ranking data factors or data values, devising scoring systems, associating scoring systems with data factors, applying scoring systems to data values (actual or ideal), producing data factor scores (actual or ideal), weighting data factor scores (actual or ideal), summing data factor scores (actual or ideal), grouping and/or averaging ideal and/or individual subject suitability scores, comparing ideal and individual scores, assessing data quality, generating data quality assessments (including study site aptitude assessments, subject suitability assessments, and/or other assessments) mining data quality information, generating remedial measures, or for performing any of the other operations described in detail herein.

In particular, data quality application 1003 may include an ideal subject suitability score module 1005a. Ideal subject suitability score module 1005a may enable the performance of operations for the generation of ideal subject suitability scores for one or more interaction points of a clinical trial according to the protocol of the clinical trial (including the operations detailed in FIGS. 2, 7, 8, and/or 9).

Data quality application 1003 may also include individual subject suitability score module 1005b. Individual subject suitability score module 1005b may enable the performance of operations for the development of one or more individual subject suitability scores according to data received from actual subject interaction with one or more interaction points of a clinical trial (including the operations detailed in FIGS. 3, 8 and 9).

Data quality application 1003 may also include a quality assessment module 1005c, which may enable the generation of a data quality assessment. Quality assessment module 1005c may also enable the performance of operations for the aggregation, averaging, and/or grouping of individual subject suitability scores and/or ideal subject suitability scores. Quality assessment module 1005c may also enable the performance of operations for the comparison of ideal and individual subject suitability scores. Quality assessment module 1005c may also enable the performance of operations for the measurement of deviations between ideal and individual subject suitability scores. Quality assessment module 1005c may enable operations for the quality assessment of data obtained from patient interaction with one or more interaction points of a clinical trial.

Data quality application 1003 may also include a data mining module 1005d. Data mining module 1005d may enable operations for the selective and/or differential assessment of clinical trial data and the identification, generation, and/or implementation of remedial measures. Data mining module may also enable retrospective analysis of individual and ideal subject suitability scores of a previously performed clinical trial for to identify one or more elements that may have caused the failure of the previously performed trial.

In some embodiments, data quality application may include an aptitude assessment module for generating a study site aptitude assessment. In other embodiments, data quality application may include a subject suitability assessment module for generating a subject suitability assessment.

Other features of the invention, including features described above may be enabled by other modules included in data quality application 1003. One or more of the modules included in data quality application 1003 may be combined. For some purposes, not all modules may be necessary.

In some embodiments, computer system 1001 may be operatively connected to one or more data storage devices 1007a-n. Data storage devices 1007a-n may be utilized to store any of the data utilized by or produced by any of the processes or functions described herein. Data storage devices 1007a-n may be, include, or interface to, for example, an Oracle™ relational database sold commercially by Oracle Corporation. Other databases, such as Informix™, DB2 (Database 2) or other data storage or query formats, platforms, or resources such as OLAP (On Line Analytical Processing), SQL (Standard Language Query), a SAN (storage area network), Microsoft Access™ or others may also be used, incorporated, or accessed into the invention.

In one embodiment, computer system 1001 may be operatively connected to one or more terminal devices 1009a-n. This operative connection may occur over a network (e.g., the Internet) or other operative connection. Communication between computer system 1001 and one or more terminal devices 1009a-n may be utilized to transmit data necessary for the implementation of the processes or functions of the invention such as, for example, entry of patient interaction data from a remote terminal device 1009a-n at a clinical trial study site for transmission to a central processing site.

One or more terminal devices 1009a-n may include a personal computer, a server, a laptop computer, a personal digital assistant (PDA), or other device. In some embodiments, one or more terminal devices 1009a-n may include a wireless terminal device.

Those having skill in the art will appreciate that the invention described herein may work with various system configurations. Accordingly, more or less of the aforementioned system components may be used and/or combined in various embodiments. It should also be understood that various software modules 1005a-n and data quality applications 1003 that are utilized to accomplish the functionalities described herein may be maintained on one or more of computer system 1001, processors 1011, terminal devices 1009a-n or other components of system 1000, as necessary. In other embodiments, as would be appreciated, the functionalities described herein may be implemented in various combinations of hardware and/or firmware, in addition to, or instead of, software.

In one embodiment, the invention may include a computer readable medium containing instructions that, when executed by at least one processor (such as, for example processor 1011 of system 1000), cause the at least one processor to enable and/or perform the features, functions, and or operations of the invention as described herein, including the any or all of the operations of the processes described in FIGS. 1, 2, 3, 7, 8, 9, and/or other operations.

While the computer readable medium and computer implemented system detailed above may be utilized for performing the methods of the invention, in some embodiments, some or all of the operations or methods of the invention may be performed manually.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A computer-implemented method for assessing data quality of clinical trial data generated during a clinical trial, wherein the clinical trial includes one or more clinical trial subjects that each interact with a plurality of data collection points of the clinical trial, the method comprising:
generating, by a processor, an ideal data quality score for a clinical trial data collected at a data collection point, wherein the data collection point comprises a point during the clinical trial at which the clinical trial data for the clinical trial is collected, wherein the clinical trial is conducted according to a clinical trial protocol that includes a protocol by which clinical trial data should be collected at the data collection point, and wherein the ideal data quality score represents a benchmark that indicates clinical trial data has been correctly collected during the data collection point in adherence to the clinical trial protocol;
receiving, by the processor, an indication of an actual procedure by which an actual clinical trial data was collected during the data collection point, wherein the actual clinical trial data is associated with a subject undergoing the clinical trial;
generating, by the processor, an individual data quality score based on one or more data factors associated with the protocol by which the clinical trial data should be collected, wherein the one or more data factors are different for different protocols by which the clinical trial data should be collected, and
wherein the one or more data factors are used to determine a level of compliance with the protocol by which the clinical trial data should be collected such that the individual data quality score represents whether the actual procedure by which the actual clinical trial data was collected from the subject at the data collection point is in adherence to the protocol by which the clinical trial data should be collected during the data collection point; and
generating, by the processor, a data quality assessment based on a comparison of the individual data quality score and the ideal data quality score, the data quality assessment representing the degree to which the protocol by which the clinical trial data should be collected was adhered to during the clinical trial.

2. The method of claim 1, wherein the ideal data quality score is based on the one or more data factors.

3. The method of claim 2, wherein the one or more data factors include data factors relevant to subject inclusion data, subject exclusion data, efficacy data, or safety data.

4. The method of claim 2, wherein generating an ideal data quality score further comprises:
associating a scoring system with each of the one or more data factors;
generating one or more ideal data factor scores by applying the scoring system associated with a data factor to an ideal data value of the data factor; and
determining the ideal data quality score based on the one or more ideal data factor scores.

5. The method of claim 2, wherein generating an ideal data quality score further comprises:
indexing the one or more data factors according to one or more characteristics;
associating a scoring system with each of the one or more data factors;
generating one or more ideal data factor scores by applying the scoring system of a data factor to an ideal data value of the data factor;
weighting the one or more ideal data factor scores; and
determining the ideal data quality score based on the weighted ideal data factor scores of the one or more data factors, wherein the ideal data quality score is determined by summing the weighted ideal data factor scores of each of the one or more data factors.

6. The method of claim 2, wherein generating an individual data quality score further comprises:
generating one or more actual data factor scores by applying a scoring system to each of one or more actual data values collected from the interaction of the at least one individual clinical trial subject with the data collection point, wherein the one or more actual data values correspond to actual data collected for each of the one more data factors on which the individual data quality score is based; and
determining the individual data quality score based on the one or more actual data factor scores.

7. The method of claim 2, wherein generating an individual data quality score further comprises:
indexing one or more actual data values according to one or more characteristics, wherein the one or more actual data values are collected from the interaction of the subject with the data collection point, and wherein the one or more actual data values correspond to actual data collected for each of the one more data factors on which the ideal data quality score is based;
generating one or more actual data factor scores by applying a scoring system to each of one or more actual data values;
weighting the one or more actual data factor scores; and
determining the individual data quality score based on the one or more weighted actual data factor scores, wherein the individual data quality score is determined by summing the one or more weighted actual data factor scores.

8. The method of claim 1, further comprising generating one or more remedial measures to improve the data quality for the data collection point based on the data quality assessment.

9. A computer-implemented method for assessing data quality of clinical trial data generated during a clinical trial, wherein the clinical trial includes one or more data collection points, involving one or more clinical trial subjects that each interact with the one or more data collection points, the method comprising:
generating, by a processor, an ideal data quality score for at least one of the one or more data collection points of the clinical trial, wherein the one or more data collection points each comprise a point during the clinical trial at which the clinical trial data for the clinical trial is collected during the clinical trial, wherein the clinical trial is conducted according to a clinical trial protocol that includes a protocol by which the clinical trial data should be collected at the one or more data collection points, and wherein the ideal data quality score for a given data collection point represents a benchmark that indicates clinical trial data has been correctly collected during the data collection point in adherence to the clinical trial protocol, and wherein the ideal data quality score for each of the at least one data collection points is generated by:
defining, by the processor, one or more data factors that are relevant to the data collection point, wherein the one or more data factors are different for different protocols by which the clinical trial data should be collected;
indexing, by the processor, the one or more data factors according to one or more characteristics, associating, by the processor, a scoring system with each of the one or more data factors, generating, by the processor, one or more ideal data factor scores by applying the scoring system associated with a data factor to an ideal data value of the data factor, weighting, by the processor, the one or more ideal data factor scores, and determining, by the processor, the ideal data quality score based on the weighted ideal data factor scores, wherein the ideal data quality score is determined by summing the weighted ideal data factor scores of each of the one or more data factors;

generating, by the processor, for each of the data collection points having an ideal data quality score, an individual data quality score for at least one of the one or more clinical trial subjects, wherein the individual data quality score represents whether actual clinical trial data was collected from the subject in adherence to the clinical trial protocol during the data collection point and is generated by:

indexing, by the processor, one or more actual data values according to one or more characteristics, wherein the one or more actual data values are collected from the interaction of the at least one individual clinical trial subject with the at least one data collection point, and wherein the one or more actual data values correspond to actual data collected for each of the one or more data factors on which the ideal data quality score is based, generating, by the processor, one or more actual data factor scores by applying the scoring system associated with each individual data factor to an actual data value of the data factor, weighting, by the processor, the actual data factor scores according to the weighted value of their corresponding ideal data factor scores, and determining, by the processor, the individual data quality score based on the one or more weighted actual data factor scores, wherein the individual data quality score is determined by summing the one or more weighted actual data factor scores and wherein the one or more actual data factor scores are used to determine a level of compliance with the clinical trial protocol such that the individual data quality score represents whether an actual procedure by which the clinical trial data was collected from the subject at the data collection point is in adherence to the clinical trial protocol; and generating, by the processor, a data quality assessment based on the individual data quality score and the ideal data quality score, wherein the data quality assessment is generated at least in part by comparing the individual data quality score to the ideal data quality score, wherein the difference between the individual data quality score and the ideal data quality score is indicative of the quality of data produced by the interaction of the at least one clinical trial subject with the data collection point, the data quality assessment representing the degree to which the clinical trial protocol was adhered to during the clinical trial.

10. A computer-implemented method for assessing a clinical trial site that enrolls one or more subjects into a clinical trial, the method comprising:

generating, by the processor, an ideal data quality score for the clinical trial site, wherein the ideal data quality score represents an ideal clinical trial site having predefined attributes suited for yielding high quality clinical trial data, and wherein the ideal data quality score is generated by:

defining, by the processor, one or more data factors that are relevant to defining the ideal clinical trial site for the clinical trial, associating, by the processor, a scoring system with each of the one or more data factors;

generating, by the processor, one or more ideal data factor scores by applying the scoring system associated with a data factor to an ideal data value of the data factor, weighting, by the processor, the one or more ideal data factor scores, and determining, by the processor, the ideal data quality score based on the one or more weighted ideal data factor scores;

generating, by the processor, a study site aptitude score for the clinical trial site by:

generating, by the processor, one or more study site data scores by applying the scoring system associated with a data factor to an actual data value for the data factor, weighting, by the processor, one or more study site data scores, and determining, by the processor, the study site aptitude score based on the one or more weighted study site data scores; and generating, by the processor, a study site aptitude assessment based on the ideal data quality score and the study site aptitude score.

11. A computer-implemented system that assesses data quality of data generated during a clinical trial, wherein the clinical trial includes one or more clinical trial subjects that each interact with a data collection point of the clinical trial, the system comprising:

one or more processors configured to:

generate an ideal data quality score for the data collection point, the data collection point comprising a point during the clinical trial at which the clinical trial data for the clinical trial is collected from the one or more clinical trial subjects during the clinical trial, wherein the clinical trial is conducted according to a clinical trial protocol that includes a protocol by which the clinical trial data should be collected at the data collection point, wherein the ideal data quality score represents a benchmark that indicates clinical trial data has been correctly collected during the data collection point in adherence to the clinical trial protocol;

receive an indication of an actual procedure by which an actual clinical trial data was collected during the data collection point, wherein the actual clinical trial data is associated with the one or more clinical trial subjects undergoing the clinical trial;

generate an individual data quality score for at least one of the one or more clinical trial subjects based on one or more data factors associated with the protocol by which the clinical trial data should be collected, wherein the one or more data factors are different for different protocols by which the clinical trial data should be collected, and wherein the one or more data factors are used to determine a level of compliance with the protocol by which the clinical trial data should be collected such that the ideal individual data quality score represents whether the actual clinical trial data was collected from the one or more individual clinical trial subjects in adherence to the clinical trial protocol during the data collection point; and generate a data quality assessment based on a comparison of the individual data quality score and the ideal data quality score, the data quality assessment representing the degree to which the clinical trial protocol was adhered to during the clinical trial.

12. The system of claim 11, wherein the one or more data factors for the data collection point are derived at least in part from a protocol associated with the clinical trial.

13. The system of claim 12, wherein the one or more data factors include data factors relevant to subject inclusion data, subject exclusion data, efficacy data, or safety data.

14. The system of claim 12, wherein the processor is further configured to:
associate a scoring system with each of the one or more data factors; and
generate one or more ideal data factor scores by application of the scoring system associated with a data factor to an ideal data value of the data factor; and
determine the ideal data quality score based on the one or more ideal data factor scores.

15. The system of claim 12, wherein the processor is further configured to:
index the one or more data factors according to one or more characteristics;
associate a scoring system with each of the one or more data factors;
generate one or more ideal data factor scores by application of the scoring system of a data factor to an ideal data value of the data factor;
weight the one or more ideal data factor scores; and
determine the ideal data quality score based on the weighted ideal data factor scores of the one or more data factors, wherein the ideal data quality score is determined by summing the weighted ideal data factor scores of each of the one or more data factors.

16. The system of claim 12, wherein the processor is further configured to:
generate one or more actual data factor scores by application of a scoring system to each of one or more actual data values collected from the interaction of the at least one of the one or more individual clinical trial subjects with the data collection point, wherein the one or more actual data values correspond to actual data collected for each of the one more data factors on which the ideal data quality score is based; and
determine the individual data quality score based on the one or more actual data factor scores.

17. The system of claim 12, wherein the processor is further configured to:
index one or more actual data values according to one or more characteristics, wherein the one or more actual data values are collected from the interaction of the at least one individual clinical trial subject with the data collection point, and wherein the one or more actual data values correspond to actual data collected for each of the one or more data factors on which the ideal data quality score is based;
generate one or more actual data factor scores by application of a scoring system to each of one or more actual data values;
weight the one or more actual data factor scores; and
determine the individual data quality score based on the one or more weighted actual data factor scores, wherein the individual data quality score is determined by summing the one or more weighted actual data factor scores.

18. The system of claim 11, wherein the processor is further configured to:
generate one or more remedial measures to improve the data quality for the data collection point based on the data quality assessment.

19. A computer-implemented system that assesses data quality of data generated during a clinical trial, wherein the clinical trial includes one or more data collection points, involving one or more clinical trial subjects that each interact with the one or more data collection points, the system comprising:
a processor configured to:
generate an ideal data quality score for at least one of the one or more data collection points of the clinical trial, a data collection point comprising a point during the clinical trial at which the clinical trial data for the clinical trial is collected from a subject, wherein the clinical trial is conducted according to a clinical trial protocol that includes a protocol by which the clinical trial data should be collected at the data collection point, wherein the ideal data quality score for a given data collection point represents a benchmark that indicates clinical trial data has been correctly collected during the data collection point in adherence to the clinical trial protocol;
define one or more data factors that are relevant to the data collection point, wherein the one or more data factors are different for different protocols by which the clinical trial data should be collected;
index the one or more data factors according to one or more characteristics;
associate a scoring system with each of the one or more data factors;
generate one or more ideal data factor scores by application of the scoring system associated with a data factor to an ideal data value of the data factor;
weight the one or more ideal data factor scores; and
determine the ideal data quality score based on the weighted ideal data factor scores, wherein the ideal data quality score is determined by summing the weighted ideal data factor scores of each of the one or more data factors;
generate, for each of the data collection points having an ideal data quality score, an individual data quality score for at least one of the one or more clinical trial subjects based on the one or more data factors, wherein the one or more data factors are used to determine a level of compliance with the protocol by which the clinical trial data should be collected such that the individual data quality score represents whether the actual procedure by which the actual clinical trial data was collected from the subject at the data collection point is in adherence to the protocol by which the clinical trial data should be collected during the data collection point;
index one or more actual data values according to one or more characteristics, wherein the one or more actual data values are collected from the interaction of the at least one individual clinical trial subject with the at least one data collection point, and wherein the one or more actual data values correspond to actual data collected for each of the one or more data factors on which the ideal data quality score is based;
generate one or more actual data factor scores by applying the scoring system associated with each individual data factor to an actual data value of the data factor;
weight the actual data factor scores according to the weighted value of their corresponding ideal data factor scores;
determine the individual data quality score based on a procedure by which actual clinical trial data was collected and the one or more weighted actual data factor scores, wherein the individual data quality score is determined by summing the one or more weighted actual data factor scores and represents whether the actual clinical trial data was collected from the subject in adherence to the clinical trial protocol during the data collection point; and generate a data quality assessment based on a comparison of the individual data quality score and the ideal data quality score, wherein the quality assessment module compares the individual data quality score to the ideal data quality score to generate the data quality assessment, and wherein the difference between the individual data quality score and the ideal data quality score is indicative of the quality of data produced by the interaction of the at least one clinical trial subject with the data collection point, the data quality assessment representing the degree to which the clinical trial protocol was adhered to during the clinical trial.

20. A computer-implemented system that assesses a clinical trial site that enrolls one or more subjects into a clinical trial, the system comprising:
a processor configured to:
generate an ideal data quality score for the clinical trial site, wherein the ideal data quality score represents an ideal clinical trial site having predefined attributes suited for yielding high quality clinical trial data;
define one or more data factors that are relevant to defining the ideal clinical trial site for the clinical trial;
associate a scoring system with each of the one or more data factors;
generate one or more ideal data factor scores by application of the scoring system associated with a data factor to an ideal data value of the data factor;
weight one or more ideal data factor scores;
determine the ideal data quality score based on the one or more weighted ideal data factor scores;
generate one or more study site data scores by application of the scoring system associated with a data factor to an actual data value for the data factor,
weight one or more study site data scores, and
determine the study site aptitude score based on the one or more weighted study site aptitude values; and
generate a study site aptitude assessment based on the ideal data quality score and the study site aptitude score.

21. A non-transitory computer readable medium containing instructions which, when executed by at least one processor, cause the at least one processor to assess data quality of data generated during a clinical trial, wherein the clinical trial includes one or more clinical trial subjects that each interact with a data collection point of the clinical trial, the instructions causing the at least one processor to:
generate an ideal data quality score for the data collection point, the data collection point comprising a point during the clinical trial at which the clinical trial data for the clinical trial is collected from a subject, wherein the clinical trial is conducted according to a clinical trial protocol that includes a protocol by which the clinical trial data should be collected at the data collection point, wherein the ideal data quality score represents a benchmark that indicates clinical trial data has been correctly collected during the data collection point in adherence to the clinical trial protocol;
receive an indication of an actual procedure by which an actual clinical trial data was collected during the data collection point, wherein the actual clinical trial data is associated with the subject undergoing the clinical trial;
generate an individual data quality score for at least one of the one or more clinical trial subjects, wherein the individual data quality score is based on one or more data factors associated with the protocol by which the clinical trial data should be collected, wherein the one or more data factors are different for different protocols by which the clinical trial data should be collected, and wherein the one or more data factors are used to determine a level of compliance with the protocol by which the clinical trial data should be collected such that the individual data quality score represents whether the actual procedure by which the actual clinical trial data was collected from the subject at the data collection point is in adherence to the protocol by which the clinical trial data should be collected during the data collection point; and generate a data quality assessment based on a comparison of the data quality score and the ideal data quality score, the data quality assessment representing the degree to which the clinical trial protocol was adhered to during the clinical trial.

22. The computer readable medium of claim 21, wherein the ideal data quality score is based on the one or more data factors relevant to the interaction point, and wherein the one or more data factors for the data collection point are derived at least in part from a protocol associated with the clinical trial.

23. The computer readable medium of claim 22, wherein the one or more data factors include data factors relevant to subject inclusion data, subject exclusion data, efficacy data, or safety data.

24. The computer readable medium of claim 22, wherein the instructions further cause the at least one processor to:
associate a scoring system with each of the one or more data factors;
generate one or more ideal data factor scores by applying the scoring system associated with a data factor to an ideal data value of the data factor; and
determine the ideal data quality score based on the one or more ideal data factor scores.

25. The computer readable medium of claim 22, wherein instructions further cause the at least one processor to:
index the one or more data factors according to one or more characteristics;
associate a scoring system with each of the one or more data factors;
generate one or more ideal data factor scores by applying the scoring system of a data factor to an ideal data value of the data factor;
weight the one or more ideal data factor scores; and
determine the ideal data quality score based on the weighted ideal data factor scores of the one or more data factors, wherein the ideal data quality score is determined by summing the weighted ideal data factor scores of each of the one or more data factors.

26. The computer readable medium of claim 22, wherein the instructions further cause the at least one processor to:
generate one or more actual data factor scores by applying a scoring system to each of one or more actual data values collected from the interaction of the at least one individual clinical trial subject with the data collection point, wherein the one or more actual data values correspond to actual data collected for each of the one or more data factors ideal data quality score; and
determine the individual data quality score based on the one or more actual data factor scores.

27. The computer readable medium of claim 22, wherein the instructions further cause the at least one processor to:
index one or more actual data values according to one or more characteristics, wherein the one or more actual data values are collected from the interaction of the at least one individual clinical trial subject with the data collection point, and wherein the one or more actual data values correspond to actual data collected for each of the one more data factors on which the ideal data quality score is based;

generate one or more actual data factor scores by applying a scoring system to each of one or more actual data values;

weight the one or more actual data factor scores; and determine the individual data quality score based on the one or more weighted actual data factor scores, wherein the individual data quality score is determined by summing the one or more weighted actual data factor scores.

28. The computer readable medium of claim 21, the instructions further causing the at least one processor to generate one or more remedial measures to improve the data quality for the data collection point based on the data quality assessment.

29. A non-transitory computer readable medium containing instructions which, when executed by at least one processor, cause the at least one processor to assess data quality of data generated during a clinical trial, wherein the clinical trial includes one or more data collection points, involving one or more clinical trial subjects that each interact with the one or more data collection points, the instructions causing the processor to:

generate an ideal data quality score for at least one of the one or more data collection points of the clinical trial, a data collection point comprising a point during the clinical trial at which data for the clinical trial is collected from a subject, wherein the clinical trial is conducted according to a clinical trial protocol that includes a protocol by which the clinical trial data should be collected at the data collection point, wherein the ideal data quality suitability score for a given data collection point represents ideal data quality from subject interaction with the given data collection point, and wherein the instructions when causing the at least one processor to generate the ideal data quality score for each of the at least one interaction data collection points, further causes the at least one processor to:

define one or more data factors that are relevant to the data collection point, wherein the one or more data factors are different for different protocols by which the clinical trial data should be collected, index the one or more data factors according to one or more characteristics, associate a scoring system with each of the one or more data factors, generate one or more ideal data factor scores by applying the scoring system associated with a data factor to an ideal data value of the data factor, weight the one or more ideal data factor scores, and determine the ideal data quality score based on the weighted ideal data factor scores, wherein the ideal data quality score is determined by summing the weighted ideal data factor scores of each of the one or more data factors;

generate, for each of the data collection points having an data quality score, an individual data quality score for at least one of the one or more clinical trial subjects, wherein the individual data quality score is generated by:

index one or more actual data values according to one or more characteristics, wherein the one or more actual data values are collected from the interaction of the at least one individual clinical trial subject with the at least one data collection point, and wherein the one or more actual data values correspond to actual data collected for each of the one or more data factors on which the ideal data quality subject score is based, generate one or more actual data factor scores by applying the scoring system associated with each individual data factor to an actual data value of the data factor, weight the actual data factor scores according to the weighted value of their corresponding ideal data factor scores, and determine the individual data quality subject score based on the one or more data factors associated with the protocol by which actual clinical trial data should be collected and the one or more weighted actual data factor scores, wherein the one or more data factors are used to determine a level of compliance with the protocol by which the clinical trial data should be collected, and wherein the individual data quality score is determined by summing the one or more weighted actual data factor scores; and generate a data quality assessment based on a comparison of the individual data quality score and the ideal data quality score, wherein the data quality assessment represents whether the clinical trial protocol was adhered to during the clinical trial and is generated at least in part by comparing the individual data quality score to the ideal data quality score, wherein the difference between the individual data quality score and the ideal data quality score is indicative of the quality of data produced by the interaction of the at least one clinical trial subject with the interaction data collection point.

30. A non-transitory computer readable medium containing instructions that, when executed by at least one processor, cause the at least one processor to assess a clinical trial site that enrolls one or more subjects into a clinical trial, by performing the operations comprising:

generating an ideal data quality score for the clinical trial site, wherein the ideal data quality score represents an ideal clinical trial site having predefined attributes suited for yielding high quality clinical trial data, and wherein the ideal data quality score is generated by:

defining one or more data factors that are relevant to defining the ideal clinical trial site for the clinical trial, associating a scoring system with each of the one or more data factors;

generating one or more ideal data factor scores by applying the scoring system associated with a data factor to an ideal data value of the data factor;

weighting one or more ideal data factor scores, and determining the ideal data quality score based on the one or more weighted ideal data factor scores;

generating a study site aptitude score for the clinical trial site by:

generating one or more study site data scores by applying the scoring system associated with a data factor to an actual data value for the data factor, weighting one or more study site data scores, and determining the study site aptitude score based on the one or more weighted study site data scores; and generating a study site aptitude assessment based on the ideal data quality score and the study site aptitude score.

31. The method of claim 1, wherein the data quality assessment is generated before or during the clinical trial.

32. The method of claim 1, wherein the data quality assessment is generated after the clinical trial has been conducted.

33. A computer-implemented method of assessing a quality of a subject for participation in a clinical trial, the clinical trial associated with a clinical trial protocol that indicates a procedure of collecting data from the subject for determining an acceptability of the subject to enter the clinical trial, the method comprising:

generating, by a processor, an ideal data quality score, wherein the ideal data quality score represents a benchmark that indicates the procedure of collecting data from the subject for determining the acceptability of the subject has been correctly followed;

receiving, by the processor, an indication of an actual procedure by which clinical trial data from the subject was collected for determining the acceptability of the subject;

generating, by the processor, an individual data quality score based on one or more data factors associated with the procedure of collecting data from the subject, wherein the one or more data factors are different for different procedures for collecting data from the subject, and wherein the one or more data factors are used to determine a level of compliance with the procedure of collecting data from the subject such that the individual data quality score represents whether the actual procedure is in adherence to the procedure of collecting data from the subject such that the individual data quality score represents whether the actual data from the subject for determining the acceptability of the subject was collected in adherence to the procedure indicated by the clinical trial protocol;

comparing, by the processor, the ideal data quality score and the individual data quality score; and generating, by the processor, a subject suitability assessment based on the comparison, wherein the subject suitability assessment represents whether the procedure for collecting data from the subject for determining the acceptability of the subject indicated by clinical trial protocol was adhered to.

\* \* \* \* \*

UNITED STATES PATENT AND TRADEMARK OFFICE
CERTIFICATE OF CORRECTION

| | | |
|---|---|---|
| PATENT NO. | : 8,682,685 B2 | Page 1 of 1 |
| APPLICATION NO. | : 11/577681 | |
| DATED | : March 25, 2014 | |
| INVENTOR(S) | : David E. Katz | |

It is certified that error appears in the above-identified patent and that said Letters Patent is hereby corrected as shown below:

In the Claims

Claim 9, column 22, line 51, delete "during the clinical trial".

Claim 11, column 24, line 37, after "trial subjects", delete "during the clinical trial".

Claim 11, column 24, line 59, after "such that the", delete "ideal".

Claim 29, column 29, line 59, after "having", change "an" to "a".

Claim 29, column 29, line 64, change "index" to "indexing".

Claim 29, column 30, line 5, change "generate" to "generating".

Claim 29, column 30, line 8, change "weight" to "weighting".

Claim 29, column 30, line 11, change "determine" to "determining".

Claim 29, column 30, line 31, delete "interaction".

Signed and Sealed this
Twenty-seventh Day of January, 2015

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,682,685 B2 |
| APPLICATION NO. | : 11/577681 |
| DATED | : March 25, 2014 |
| INVENTOR(S) | : Katz |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1206 days.

Signed and Sealed this
Twenty-first Day of July, 2015

Michelle K. Lee
*Director of the United States Patent and Trademark Office*